United States Patent
Miller et al.

(10) Patent No.: US 9,733,168 B2
(45) Date of Patent: *Aug. 15, 2017

(54) MANIPULATION OF MICROFLUIDIC DROPLETS

(71) Applicant: Raindance Technologies, Inc., Billerica, MA (US)

(72) Inventors: Benjamin Miller, Littleton, MA (US); Brian Hutchison, Medford, MA (US); Andrew Wilson, Arlington, MA (US); Jonathan William Larson, Chelsea, MA (US); Qun Zhong, Lexington, MA (US); Yevgeny Yurkovetsky, Winchester, MA (US); Darren Link, Lexington, MA (US); Mark Weary, North Billerica, MA (US)

(73) Assignee: Raindance Technologies, Inc., Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/082,424

(22) Filed: Mar. 28, 2016

(65) Prior Publication Data

US 2016/0209303 A1   Jul. 21, 2016

Related U.S. Application Data

(63) Continuation of application No. 14/511,892, filed on Oct. 10, 2014, now Pat. No. 9,341,594, which is a
(Continued)

(51) Int. Cl.
*F16K 99/00* (2006.01)
*G01N 1/38* (2006.01)
(Continued)

(52) U.S. Cl.
CPC .............. *G01N 1/38* (2013.01); *B01L 3/0241* (2013.01); *B01L 3/502715* (2013.01);
(Continued)

(58) Field of Classification Search
CPC .............. B01L 3/0241; B01L 3/502784; B01L 3/502715; B01L 2200/061;
(Continued)

(56) References Cited

U.S. PATENT DOCUMENTS 6,664,044 B1 * 12/2003 Sato .................... B01J 19/0046
422/68.1
7,227,621 B2 * 6/2007 Lee .......................... G01F 1/00
356/28

(Continued)

FOREIGN PATENT DOCUMENTS

WO   WO 2009005680 A1 *  1/2009   ........ B01L 3/502761
WO   WO 2009029229 A2 *  3/2009   ............ B01F 3/0807

OTHER PUBLICATIONS

Nguyen NT et al: "Optical detection fordroplet size control in microfluidic droplet-based analysis systems" Sensors and Actuators B, Elsevier Sequoias. A., Lausanne, CH LNKD-DOI: 10.1016/J.SNB.2005.12.010 vol. 117, No. 2, Oct. 12, 2006 (Oct. 12, 2006), pp. 431-436, XP025112307.*

(Continued)

*Primary Examiner* — Matthew W Jellett
(74) *Attorney, Agent, or Firm* — Brown Rudnick LLP; Thomas C. Meyers

(57) ABSTRACT

The invention provides methods for assessing one or more predetermined characteristics or properties of a microfluidic droplet within a microfluidic channel, and regulating one or more fluid flow rates within that channel to selectively alter the predetermined microdroplet characteristic or property using a feedback control.

14 Claims, 11 Drawing Sheets

Related U.S. Application Data continuation of application No. 14/021,481, filed on Sep. 9, 2013, now Pat. No. 8,857,462, which is a continuation of application No. 12/729,462, filed on Mar. 23, 2010, now Pat. No. 8,528,589.

(60) Provisional application No. 61/162,521, filed on Mar. 23, 2009.

(51) Int. Cl.
  *B01L 3/02* (2006.01)
  *B01L 3/00* (2006.01)
  *F17D 3/01* (2006.01)
  *G01N 27/447* (2006.01)
  *G01N 21/03* (2006.01)

(52) U.S. Cl.
  CPC .... *B01L 3/502784* (2013.01); *F16K 99/0001* (2013.01); *F17D 3/01* (2013.01); *G01N 27/44791* (2013.01); *B01L 2200/061* (2013.01); *B01L 2200/0673* (2013.01); *B01L 2200/143* (2013.01); *B01L 2300/0877* (2013.01); *F16K 2099/0084* (2013.01); *G01N 2021/0353* (2013.01); *Y10T 137/2185* (2015.04); *Y10T 137/7761* (2015.04); *Y10T 137/8158* (2015.04); *Y10T 137/8593* (2015.04); *Y10T 436/118339* (2015.01)

(58) Field of Classification Search
  CPC ....... B01L 2200/0673; B01L 2200/143; G01N 27/44791; G01N 1/38; G01N 2021/0353; F16K 99/0001; F16K 2099/0084; Y10T 137/7761; Y10T 436/118339
  See application file for complete search history.

(56) References Cited

U.S. PATENT DOCUMENTS

| | | | | |
|---|---|---|---|---|
| 7,617,070 | B2* | 11/2009 | Kurth | G01C 21/025 702/150 |
| 7,955,864 | B2* | 6/2011 | Cox | B01L 3/502715 137/565.01 |
| 8,528,589 | B2* | 9/2013 | Miller | B01L 3/0241 137/487.5 |
| 8,857,462 | B2* | 10/2014 | Miller | B01L 3/0241 137/487.5 |
| 9,341,594 | B2* | 5/2016 | Miller | B01L 3/0241 |
| 2010/0255556 | A1* | 10/2010 | Hunt | B01L 3/502761 435/173.1 |
| 2010/0304378 | A1* | 12/2010 | Griffiths | C12N 15/1086 435/6.14 |

OTHER PUBLICATIONS

Kai-Liang et al: "DEP actuated nanoliter droplet dispensing using feedback control" Lab on a Chip, vol. 9, Dec. 24, 2008 (Dec. 24, 2008), pp. 901-909, XP002584446.*

* cited by examiner

MANIPULATION OF MICROFLUIDIC DROPLETS

CROSS-REFERENCE TO RELATED APPLICATIONS

This application is a continuation of U.S. Nonprovisional application Ser. No. 14/511,892, filed Oct. 10, 2014, which is a continuation of U.S. Nonprovisional application Ser. No. 14/021,481, filed Sep. 9, 2013, now U.S. Pat. No. 8,857,462, which is a continuation of U.S. Nonprovisional application Ser. No. 12/729,462, filed Mar. 23, 2010, now U.S. Pat. No. 8,528,589, which claims the benefit of U.S. Provisional Application No. 61/162,521, filed Mar. 23, 2009. Each of which is incorporated herein by reference.

FIELD OF THE INVENTION

The invention relates to the control and manipulation of microdroplets within microchannels.

BACKGROUND OF THE INVENTION

Methods for generating microdroplets of a uniform volume at a regular frequency are well known in the art. However, sample to sample variations in viscosity, viscoelasticity, surface tension or other physical properties of the sample fluid coming from, but not limited to, the inclusion of polymers, detergents, proteins, cells, nucleic acids or buffering solutions, influence the droplet size and volume and, hence, the frequency of generation in an unpredictable way. Thus, the same nozzle on the same microfluidic substrate with same carrier fluid, but a different dispersed fluid will result in a different droplet volume at a different frequency. These limitations also have an impact on the extent to which volumes can be reproducibly combined. Together with typical variations in pump flow rate precision and variations in channel dimensions, microfluidic systems are severely limited without a means to compensate on a run-to-run basis.

As a result of the above factors, current microdroplet technologies cannot efficiently or reliably be used for applications involving combining droplets of different species at high frequencies. Consequently, there is a need in the art for methods of precise control, manipulation and regulation of droplet frequency generation, frequency of library droplet introduction and droplet volume.

SUMMARY OF THE INVENTION

The present invention provides a feedback control system for microfluidic droplet manipulation comprising: providing a microfluidic system comprising at least one microfluidic channel containing at least one fluidic droplet; detecting at least one predetermined characteristics of said fluidic droplet at one or more positions within said microfluidic channel; assessing said predetermined characteristic using an image sensor; and transmitting said assessment from said image sensor to a feedback controller, wherein said feedback controller adjusts a flow rate of one or more fluids, thereby manipulating said fluidic droplet within said microfluidic channel. The detecting at least one predetermined characteristics of said fluidic droplet at one or more positions within said microfluidic channel can further comprises acquiring a plurality of images of said fluidic droplet at a plurality of time points within said microfluidic channel, wherein said plurality of images comprises an image set.

The system can further include: assessing said predetermined characteristic of said fluidic droplet in said microfluidic channel, within each image set, using an image sensor; comparing said assessment of said predetermined characteristic of said fluidic droplet in each image set; and determining an average assessment of said predetermined characteristic of said fluidic droplet; wherein said feedback controller adjusts a flow rate of one or more fluids, thereby increasing the accuracy of the assessment.

The predetermined characteristic can be droplet volume, droplet generation rate, droplet arrival frequency, droplet release rate, or total droplet count. The one or more fluids can be a carrier fluid or a drive fluid.

The present invention also provides a feedback control system for manipulating microfluidic droplet pairing ratios comprising: providing a microfluidic system comprising at least one microfluidic channel; producing a first plurality of fluidic droplets within said microfluidic channel at a first frequency; producing a second plurality of fluidic droplets within said microfluidic channel at a second frequency, wherein at least one fluidic droplet from said first plurality and at least one fluidic droplet from said second plurality are paired; assessing said first frequency and said second frequency using an image sensor; and transmitting said assessment of said first and said second frequency from the image sensor to a feedback controller; wherein said feedback controller adjusts a flow rate of one or more fluids to provide a desired frequency ratio of said first to said second plurality of droplets, thereby manipulating the pairing ratios of said first and second pluralities of fluidic droplets within said microfluidic channel. The first plurality of fluidic droplets and the second plurality of fluidic droplets were introduced at the same frequency and wherein said feedback controller adjusts a flow rate of one or more fluids to maintain said first and said second frequency at the same frequency.

The first and second pluralities of fluidic droplets can differ in size, color, refractive index, or extinction coefficient. The first and second pluralities of fluidic droplets can contain a different biological, biochemical, or chemical entity. The desired frequency ratio of the first plurality of droplets to the second plurality of droplets can be 1:1, 1:2, 1:3, 1:4, 1:5, 1:6, 1:7, 1:8, 1:9, or 1:10. Preferably, the desired frequency ratio of the first plurality of droplets to the second plurality of droplets is 1:1.

The present invention also provides a feedback control system for controlling microfluidic droplet count comprising: providing a microfluidic system comprising at least one microfluidic channel; producing at least a first plurality of fluidic droplets within said microfluidic channel at a first frequency; assessing said first frequency using an image sensor; determining the time required to produce a predetermined amount of fluidic droplets based upon said frequency assessment; and transmitting said assessment to a feedback controller, wherein said feedback controller stops said introduction of said droplets after said determined time, thereby controlling the microfluidic droplet count.

The present invention also provides a feedback control system for independently controlling microfluidic droplet volume and frequency comprising: providing a microfluidic system comprising at least one microfluidic channel; producing a plurality of fluidic droplets within a carrier fluid within said microfluidic channel using a drive fluid; assessing the frequency, volume, and flow rate of said plurality of droplets using an image sensor; transmitting said assessed frequencies, volumes, and flow rates of the plurality of droplets from said image sensor to a feedback controller; adjusting a flow rate of the carrier fluid using said feedback controller to attain a predetermined droplet frequency set point; and adjusting a flow rate of the drive fluid using said feedback controller to attain a predetermined droplet volume set point; wherein said feedback control system independently determines and controls microfluidic droplet frequency and volume. The plurality of fluidic droplets can be generated within the microfluidic channel. The plurality of fluidic droplets can be pre-formed and introduced to the microfluidic channel.

The invention provides a feedback control system for microfluidic droplet manipulation including: (a) detecting one or more predetermined characteristics of a droplet at one or more positions within a microfluidic channel; (b) assessing the predetermined characteristic using an image sensor; and (c) transmitting the assessment from the image sensor to a feedback controller, wherein the feedback controller adjusts a flow rate of one or more fluids, thereby manipulating the droplet within the microfluidic channel. In one aspect of this system, the predetermined characteristic is droplet volume, droplet generation rate, droplet release rate, or total droplet count. Preferably, the predetermined characteristic is droplet volume. In another aspect of this system, the fluid is a carrier fluid or a drive fluid.

The invention also provides a feedback control system for manipulating microfluidic droplet pairing ratios including: (a) producing a first plurality of droplets within a microfluidic channel at a frequency; (b) assessing the frequency of the first-plurality of droplets using an image sensor; (c) producing a second plurality of droplets within a microfluidic channel at the same frequency as the first plurality of droplets; (d) assessing the frequency of the second plurality of droplets using an image sensor; and (e) transmitting the frequencies of the first and second pluralities of droplets from the image sensor to a feedback controller; wherein the feedback controller adjusts a flow rate of one or more fluids to maintain the first and second pluralities of droplets at identical frequencies, thereby manipulating the pairing ratios of the first and second pluralities of droplets within the microfluidic channel. In one aspect of this system, the first and second pluralities of droplets differ in size, color, refractive index, or extinction coefficient. Alternatively, or in addition, the first and second pluralities of droplets contain a different biological, biochemical, or chemical entity. In another aspect of this system, the fluid is a carrier fluid or a drive fluid.

Furthermore, the invention provides a feedback control system for assessing and manipulating a predetermined characteristic of a microfluidic droplet including: (a) acquiring a plurality of images of a droplet at a plurality of time points within a microfluidic channel, wherein said plurality of images comprises an image set; (b) assessing the predetermined characteristic of the droplet in the microfluidic channel using an image sensor; and (c) transmitting the assessment from the image sensor to a feedback controller, wherein the feedback controller adjusts a flow rate of one or more fluids, thereby manipulating the predetermined characteristic of the droplet within the microfluidic channel. In one aspect, this system further includes: (a) acquiring a plurality of image sets at a plurality of time points; (b) assessing the predetermined characteristic of the droplet in the microfluidic channel, within each image set, using an image sensor; (c) comparing the assessment of the predetermined characteristic of the droplet in each image set; and (d) determining an average assessment of the predetermined characteristic of the droplet; wherein the feedback controller adjusts a flow rate of one or more fluids, thereby increasing the accuracy of the assessment. In another aspect of this system, the predetermined characteristic is droplet arrival frequency or droplet volume. Moreover, the fluid of this system is a carrier fluid or a drive fluid.

The invention provides a feedback control system for independently controlling microfluidic droplet volume and frequency including: (a) producing a plurality of droplets within a microfluidic channel; (b) assessing the droplet frequency, volume, and flow rate of the plurality of droplets using an image sensor; (c) transmitting the frequencies, volumes, and flow rates of the plurality of droplets from the image sensor to a feedback controller; (d) adjusting a flow rate of the carrier fluid using a feedback controller to attain a predetermined droplet frequency set point; and (e) adjusting a flow rate of a drive fluid using a feedback controller to attain a predetermined droplet volume set point; wherein the feedback control system independently determines microfluidic droplet frequency and volume.

The invention further provides a feedback control system for manipulating microfluidic droplet pairing ratios including: (a) producing a first plurality of droplets within a microfluidic channel at a frequency; (b) assessing the frequency of the first-plurality of droplets using an image sensor; (c) producing a second plurality of droplets within a microfluidic channel at a second frequency; (d) assessing the frequency of the second plurality of droplets using an image sensor; and (e) transmitting the frequencies of the first and second pluralities of droplets from the image sensor to a feedback controller; wherein the feedback controller adjusts a flow rate of one or more fluids to produce a desired frequency ratio of the first to the second plurality of droplets, thereby manipulating the pairing ratios of the first and second pluralities of droplets within the microfluidic channel. In one aspect of this system, the desired frequency ratio of the first plurality of droplets to the second plurality of droplets is 1:1. Alternatively, the desired frequency ratio of the first plurality of droplets to the second plurality of droplets is selected from the group consisting of 1:1, 1:2, 1:3, 1:4, 1:5, 1:6, 1:7, 1:8, 1:9, and 1:10. Alternatively, or in addition, each droplet of the first plurality of droplets comprises a single element of a genomic library and each droplet the second plurality of droplets comprises a single primer pair.

The invention provides a feedback control system for controlling microfluidic droplet count including: (a) producing at least a first plurality of droplets within a microfluidic channel at a frequency; (b) assessing the frequency of the first-plurality of droplets using an image sensor; (c) determining the time required to produce a predetermined amount of droplets based upon the frequency assessment; and (d) transmitting the assessment to a feedback controller, wherein the feedback controller stops production of the droplets after the determined time, thereby controlling the microfluidic droplet count.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

DETAILED DESCRIPTION OF THE INVENTION

Figure 1:
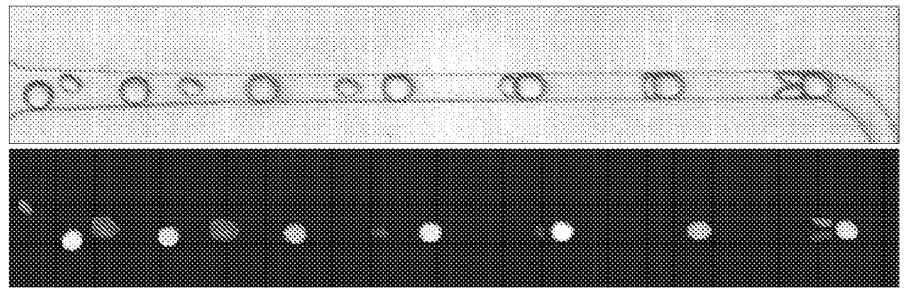
FIG. 1 is a photograph of a series of images of two fluidic droplets paired within a microfluidic channel. One droplet is from a first plurality of droplets at one size and the second droplet is from a second plurality of droplets and a different size than the droplet from the first plurality. This representative image shows the droplet from the first plurality and the droplet from the second plurality paired in a 1:1 ratio. The top panel shows droplets in the region of interest (ROI) and the bottom panel shows the corresponding "contour accumulator image," in which the grey level intensity corresponds to the number of times each pixel was added to the accumulator image. In the bottom panel, all other pixels were assigned the value "0", which is shown as black.

The methods of the present invention provide precise and highly regulated control of microfluidic droplet movement and interaction within a microfluidic channel. The invention provides a feedback control system for microfluidic droplet manipulation including: (a) providing a microfluidic system comprising at least one microfluidic channel containing at least one fluidic droplet; (b) detecting at least one predetermined characteristics of the fluidic droplet at one or more positions within the microfluidic channel; (c) assessing the predetermined characteristic using an image sensor; and (d) transmitting the assessment from the image sensor to a feedback controller, wherein the feedback controller adjusts a flow rate of one or more fluids, thereby manipulating the fluidic droplet within the microfluidic channel. The manipulating or controlling a droplet or a plurality of droplets within a microfluidic channel includes, but is not limited to, manipulating an absolute or relative droplet volume, a droplet pairing ratio, a droplet frequency, a droplet frequency ratio, the number of droplets generated and/or a droplet count. The terms manipulating and controlling are used interchangeably herein.

The present invention also provides feedback control system for assessing and manipulating a predetermined characteristic of a microfluidic droplet including: (a) providing a microfluidic system comprising at least one microfluidic channel containing at least one fluidic droplet; (b) acquiring a plurality of images of the fluidic droplet at a plurality of time points within the microfluidic channel, wherein the plurality of images comprises an image set; (c) assessing the predetermined characteristic of the fluidic droplet in the microfluidic channel using an image sensor; and (d) transmitting the assessment from the image sensor to a feedback controller, wherein the feedback controller adjusts a flow rate of one or more fluids, thereby manipulating the predetermined characteristic of the fluidic droplet within the microfluidic channel. The system can further include: assessing said predetermined characteristic of said fluidic droplet in said microfluidic channel, within each image set, using an image sensor; comparing said assessment of said predetermined characteristic of said fluidic droplet in each image set; and determining an average assessment of said predetermined characteristic of said fluidic droplet; wherein said feedback controller adjusts a flow rate of one or more fluids, thereby increasing the accuracy of the assessment.

Microdroplets are essentially miniaturized test tubes with a volume of less than 1 pico-liter (one trillionth of a liter) to several hundred nanoliters (one billionth of a liter). Because of their incredibly small size, each microdroplet requires only a very small amount of sample to conduct chemical reactions, biological assays and medical testing, thus yielding a wealth of information for biomedical and chemical studies from very limited source material at relatively low cost, e.g., a 10 micro-liter sample can be used for 1 million reactions with each reaction using 10 pico-liters. Furthermore, microdroplets can be introduced into microfluidic devices, which feature a series of micrometer-sized channels etched or molded into a chip where microdroplets can be manipulated by directing the flow of the fluids that carry them. The term "carrier fluid" or "carrier fluids" refers to any fluid which contains droplets and transports them through microfluidic channels of microfluidic devices. Carrier fluids are described in greater detail herein.

In microfluidic devices, microdroplets can be processed, analyzed and sorted at a highly efficient rate of several thousand droplets per second, providing a powerful platform which allows rapid screening of millions of distinct compounds, biological probes, proteins or cells either in cellular models of biological mechanisms of disease, or in biochemical, or pharmacological assays. Although major improvements in regulating droplet size and uniformity, and modifying droplet surface chemistry have been achieved, the utility of microdroplets in chemistry, biology, and medicine depends critically on the spatiotemporally precise delivery of microdroplets of various properties through the channels in microfluidic devices.

In order to utilize microdroplets for rapid large-scale chemical screening or complex biological library identification, different species of microdroplets, each containing the specific chemical compounds or biological probes of interest, have to be generated and combined at the preferred conditions, e.g., mixing ratio and order of combination. For example, one microdroplet of species A must be combined with one microdroplet of species B, but not with two microdroplets of species B or with one microdroplet of species C. The ratio of combining different species of microdroplets is achieved by adjusting the frequencies at which microdroplets are delivered to the site of combination. The terms "frequency" or "frequencies" refer to the rate at which microdroplets of certain species are delivered to a specific location. Moreover, this frequency or rate is a number per unit time, typically several hundred to tens of thousands per second. Furthermore the terms "frequency" or "frequencies" refers to the number of times at which droplets of certain species are delivered to a specific location. The location can be where certain behaviors of droplets (e.g., pairing, merging, combination, etc.) occur or where certain actions (e.g., electrification, mechanical deformation, etc.) are applied to droplets. Preferably, the location is where combination of droplets occurs.

Preferably, each species of droplet is introduced at a confluence point in a main microfluidic channel from separate inlet microfluidic channels. Preferably, droplet volumes are chosen by design such that one species is larger than others and moves at a different speed, usually slower than the other species, in the carrier fluid, as disclosed in U.S. Publication No. US 2007/0195127 and International Publication No. WO 2007/089541, each of which are incorporated herein by reference in their entirety. The channel width and length is selected such that faster species of droplets catch up to the slowest species. Size constraints of the channel prevent the faster moving droplets from passing the slower moving droplets resulting in a train of droplets entering a merge zone. In the merge zone, droplets are induced to coalesce into a single droplet, preferably an electric field is utilized to induce coalescence. Multi-step chemical reactions, biochemical reactions, or assay detection chemistries often require a fixed reaction time before species of different type are added to a reaction. Multi-step reactions are achieved by repeating the process multiple times with a second, third or more confluence points each with a separate merge point. Highly efficient and precise reactions and analysis of reactions are achieved when the frequencies of droplets from the inlet channels are matched to an optimized ratio and the volumes of the species are matched to provide optimized reaction conditions in the combined droplets.

Key elements for using microfluidic channels to process droplets include: (1) producing droplet of the correct volume, (2) producing droplets at the correct frequency and (3) bringing together a first stream of sample droplets with a second stream of sample droplets in such a way that the frequency of the first stream of sample droplets matches the frequency of the second stream of sample droplets. Preferably, bringing together a stream of sample droplets with a stream of premade library droplets in such a way that the frequency of the library droplets matches the frequency of the sample droplets.

Methods for producing droplets of a uniform volume at a regular frequency are well known in the art. One method is to generate droplets using hydrodynamic focusing of a dispersed phase fluid and immiscible carrier fluid, such as disclosed in U.S. Publication No. US 2005/0172476 and International Publication No. WO 2004/002627. Feedback on the infusion rates of the carrier fluid and the dispersed fluid provides droplets that are uniform in size and generated at a fixed frequency over arbitrarily long periods of time. However, sample to sample variations in viscosity, viscoelasticity, surface tension or other physical properties of the sample fluid coming from but not limited to the inclusion of polymers, detergents, proteins, cells, nucleic acids or buffering solutions, influence the droplet size, and, hence, frequency of generation in an unpredictable way, generating a significant problem to be solved. Hence, the same nozzle on the same substrate with same carrier fluid, but a different dispersed fluid will result in a different droplet volume at a different frequency. Moreover, often it is desirable for one of the species introduced at the confluence to be a pre-made library of droplets where the library contains a plurality of reaction conditions, e.g., a library can contain plurality of different compounds at a range of concentrations encapsulated as separate library elements for screening their effect on cells or enzymes, alternatively a library could be composed of a plurality of different primer pairs encapsulated as different library elements for targeted amplification of a collection of loci, alternatively a library could contain a plurality of different antibody species encapsulated as different library elements to perform a plurality of binding assays. The introduction of a library of reaction conditions onto a substrate is achieved by pushing a premade collection of library droplets out of a vial with a drive fluid. The drive fluid is a continuous fluid. The drive fluid may comprise the same substance as the carrier fluid (e.g., a fluorocarbon oil). For example, if a library consists of ten pico-liter droplets is driven into a inlet channel on a microfluidic substrate with a drive fluid at a rate of 10,000 pico-liters per second, then nominally the frequency at which the droplets are expected to enter the confluence point is 1000 per second. However, in practice droplets pack with oil between them that slowly drains. Over time the carrier fluid drains from the library droplets and the number density of the droplets (number/mL) increases. Hence, a simple fixed rate of infusion for the drive fluid does not provide a uniform rate of introduction of the droplets into the microfluidic channel in the substrate. Moreover, library-to-library variations in the mean library droplet volume result in a shift in the frequency of droplet introduction at the confluence point. Thus, the lack of uniformity of droplets that results from sample variation and oil drainage provides another problem to be solved. For example if the nominal droplet volume is expected to be 10 pico-liters in the library, but varies from 9 to 11 pico-liters from library-to-library then a 10,000 pico-liter/second infusion rate will nominally produce a range in frequencies from 900 to 1,100 droplet per second. In short, sample to sample variation in the composition of dispersed phase for droplets made on chip, a tendency for the number density of library droplets to increase over time and library-to-library variations in mean droplet volume severely limit the extent to which frequencies of droplets can be reliably matched at a confluence by simply using fixed infusion rates. In addition, these limitations also have an impact on the extent to which volumes can be reproducibly combined. Combined with typical variations in pump flow rate precision and variations in channel dimensions, systems are severely limited without a means to compensate on a run-to-run basis. The foregoing facts not only illustrate a problem to be solved, but also demonstrate a need for a method of instantaneous regulation of microfluidic control over microdroplets within a microfluidic channel.

As a result of the above factors, current microdroplet technologies cannot efficiently or reliably be used for applications involving combining droplets of different species at high frequencies. Consequently, there is a need in the art for novel methods of manipulating droplet frequency of generation, frequency of library droplet introduction and droplet volume.

It is well established to one of ordinary skill in the art that objects and geometrical properties of objects are identified from standard image acquisition and machine vision protocols. For example, objects in images of microfluidic channels such as droplets, channel walls, or contaminating particulate are readily distinguished and classified by their boundary, projected area, and ellipticity of the objects.

The invention provides a method for capturing images of objects within microfluidic channels such as microdroplets and channel walls, collecting the information to measure and assess both frequency and volume, and subsequently changing the infusion rates to match specific set points. The benefit of using image processing to measure droplet parameters in-situ allows system requirements such as pump flow rate accuracy and microfluidic channel tolerances to be relaxed. Thus, image processing protocols provide the practical advantage of reducing the system cost.

The invention provides a feedback control system for microfluidic droplet manipulation of one or more predetermined properties or characteristics of a microdroplet. One embodiment of the invention is directed to a system for dynamically measuring or assessing, and controlling or manipulating droplets via machine vision for feedback measurement and adjusting fluid flow rates to manipulate one or more predetermined properties or characteristics of a microdroplet. Examples of controllable droplet properties or characteristics include, but are not limited to, droplet volume, droplet generation rate, droplet release rate, and the total number of droplets generated. Preferably the selective manipulation occurs with droplets in a microfluidic device. Such microfluidic devices are generally known in the art. Exemplary preferred microfluidic devices are provided by U.S. Publication No. US 2008/0003142, International Publication No. WO 2008/063227, U.S. Publication No. US 2008/0014589, and International Publication No. WO 2007/081385, each of which are incorporated herein by reference in their entirety. Flow rates are adjusted by a drive infusion system that is not constrained to a defined technology or mechanism. Methods of the invention encompass art-recognized drive infusion systems, including those systems disclosed in U.S. Publication No. US 2008/0003142, International Publication No. WO 2008/063227, U.S. Publication No. US 2008/0014589, and International Publication No. WO 2007/081385. Furthermore, exemplary drive infusion systems of the methods of the invention include, but are not limited to, a syringe pump, pressure head, electrokinetic drive or any other means known in the art.

Figure 3:
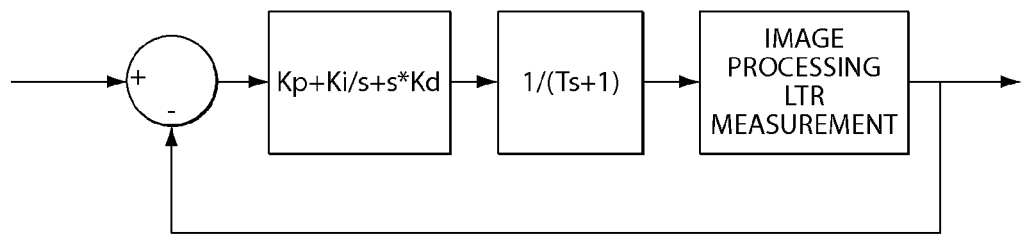
FIG. 3 is a schematic diagram of "feedback control," in which system inputs are adjusted according to measured system outputs.

"Feedback control," as shown in FIG. 3, refers to adjusting system inputs according to measured, assessed, characterized, or determined system outputs. Exemplary system outputs include, but are not limited to, the image processing LTR measurement, an assessment from an image scanner (a measurement of size, speed, frequency, refractive index, extinction coefficient, color, volume, area, number, phase, coalescence, or a determination of the contents of a microfluidic droplet), a characteristic or property of a microfluidic droplet or plurality of droplets (size, speed, frequency, refractive index, extinction coefficient, color, volume, area, number, phase, coalescence, content or activity thereof, fluorescence, or any change thereof), a characteristic or property of a fluid within a microfluidic channel (content, viscosity, surface tension, clarity, opacity, thickness, shear forces, speed, volume, pressure, temperature, and solubility), and a characteristic or property of the microfluidic device itself Exemplary system inputs include, but are not limited to, a microfluidic droplet or a plurality of microfluidic droplets, one or more fluids, automated instructions transmitted to one or more pumps or devices that control a fluid within a microfluidic device, or automated instructions transmitted to one or more pumps or devices that control to introduction of droplets into a microfluidic channel or the production, generation, or creation of a microfluidic droplet within a microfluidic channel of a microfluidic device. System outputs are assessed, and signals or instructions are transmitted from a feedback controller to a device that controls a system input. The feedback controller adjusts system input either in response to changing system outputs to maintain a constant state of efficiency or to manipulate a microfluidic droplet or plurality of droplets.

The present invention provides methods to selectively measure or assess and manipulate the absolute or relative droplet volume. The relative droplet volume can be determined by analysis of an image captured by an image scanner. This analysis includes capturing an image of a droplet, or a plurality of droplets, at a point in a microfluidic channel containing a lithographically inscribed size marker, such as a circle or a square; determining the number of image pixels occupied by a droplet and by the size marker; and comparing the resultant pixel numbers to determine a relative droplet volume. Absolute droplet volume is determined by dividing a flow rate, such as the infusion flow rate, represented as Q, by the droplet frequency, represented by v, in the following equation:

$$\overline{V} = \frac{Q}{v}.$$

In one example, the droplet volume is controlled by adjusting the drive fluid through feedback control based on the droplet projected area as measured by an image sensor. In a preferred embodiment of this method, the image sensor is a digital image sensor. In another example, the droplet volume is controlled by adjusting the drive fluid through feedback control based upon the droplet volume, as measured or assessed by Pulsed Illumination Scanning (PILS).

The present invention also provides methods to selectively manipulate droplet pairing ratios. The present invention provides a feedback control system for manipulating microfluidic droplet pairing ratios including: (a) providing a microfluidic system comprising at least one microfluidic channel; (b) introducing a first plurality of fluidic droplets within the microfluidic channel at a first frequency; (c) introducing a second plurality of fluidic droplets within the microfluidic channel at a second frequency, wherein at least one fluidic droplet from the first plurality and at least one fluidic droplet from the second plurality are paired; (d) assessing the first frequency and the second frequency using an image sensor; and (e) transmitting the assessment of the first and the second frequency from the image sensor to a feedback controller; wherein the feedback controller adjusts a flow rate of one or more fluids to maintain the first and the second frequency at the same frequency, thereby manipulating the pairing ratios of the first and second pluralities of fluidic droplets within the microfluidic channel. The present invention also provides a feedback control system for manipulating microfluidic droplet pairing ratios including: (a) providing a microfluidic system comprising at least one microfluidic channel; (b) introducing a first plurality of fluidic droplets within the microfluidic channel at a first frequency; (c) introducing a second plurality of fluidic droplets within the microfluidic channel at a second frequency; (d) assessing the first frequency and the second frequency using an image sensor; and (e) transmitting the assessment of the first and the second frequency from the image sensor to a feedback controller; wherein the feedback controller adjusts a flow rate of one or more fluids to provide a desired frequency ratio of the first to the second plurality of droplets, thereby manipulating the pairing ratios of the first and second pluralities of fluidic droplets within the microfluidic channel.

The frequencies of a first droplet and a second droplet, or a first plurality and a second plurality of droplets, are controlled relative to each other to have the same frequency but out of phase such that the droplets are intercalated, or interdigitated, (and thus paired) when traveling through the microfluidic channel. A first plurality of droplets and a second plurality of droplets having identical or matched frequencies, and which enter a microfluidic channel at the same time, are out-of-phase when either the first or second plurality of droplets travel down the microfluidic channel at a different speed from the other. As such, the droplets of the first and second pluralities intercalate, or interdigitate, because they do not travel together. In a preferred embodiment, the frequencies of the first and second pluralities are not identical, but rather matched, such that intercalation, or interdigitation, of the droplets still occurs. For example, the frequency of a second plurality of droplets that is matched to the frequency of a first plurality of droplets is greater to or less than the frequency of the first plurality by approximately 1, 10, 100, or 1000 Hz, or any point in between.

The present invention further provides methods to selectively manipulate the number of droplets generated. In one example, the system counts the number of droplets generated and stops pump flow once the desired number of droplets is reached. Thus, the present invention provides a feedback control system for controlling microfluidic droplet count including: (a) providing a microfluidic system comprising at least one microfluidic channel; (b) introducing at least a first plurality of fluidic droplets within the microfluidic channel at a first frequency; (c) assessing the first frequency using an image sensor; (d) determining the time required to produce a predetermined amount of fluidic droplets based upon the frequency assessment; and (e) transmitting the assessment to a feedback controller, wherein the feedback controller stops the introduction of the droplets after the determined time, thereby controlling the microfluidic droplet count.

The present invention provides a process including droplet detection, droplet assessment and characterization, and feedback control, for selectively manipulating the various droplet properties or characteristics in a microfluidic device.

Machine vision provides a means to accurately detect and characterize properties of droplets. Droplet characterization is then used to adjust the fluidic system inputs, fluid flow rates and drive infusion flow rates to manipulate the droplet characteristics or properties. These characterization and control schemes are applied in parallel, for example frequency, droplet diameter and droplet pairing are controlled at the same time. Alternatively, these characterization and control schemes are applied in series, for example frequency, droplet diameter and droplet pairing are controlled sequentially.

The invention provides a method for measuring and controlling the arrival frequency of regularly separated objects, e.g. droplets, including the measurement of multiple images acquired at different times (e.g. image sets) to measure the displacement of the objects, and acquisition of different image sets at varying times between images to reduce the uncertainty in the measurement. Methods of the invention accurately and inexpensively measure droplet frequency and volume. The present invention provides methods to selectively manipulate the frequency of droplets generated and released by adjusting the flow rate of a fluid, for example, the carrier fluid or drive fluid. In one example, the flow rate of the carrier fluid and drive fluid is adjusted in response to detecting the distance a single droplet moves during a known quantity of time, e.g. as determined by Pulsed Illumination Scanning.

"Droplet pairing" refers to the process of interleaving different classes of droplets at a time variant ratio (e.g. user settable function or constant value). The ratio is defined as x droplets of species A for every droplet of species B. In one example, two different classes of droplets are intercalated, or interdigitated, wherein the droplets differ in size (e.g., diameter, perimeter, diagonal, volume, area of cross-section etc), shape (e.g., spherical, elliptical, rectangular, etc.), color, refractive index or extinction coefficient. The term "refractive index" refers to the ability of a medium (e.g., glass, air, solution, etc.) to reduce the speed of waves (e.g., light, radio wave, sound wave, etc.) traveling inside the medium. The term "extinction coefficient" refers to the strength of a medium (e.g., glass, air, solution, etc.) to absorb or scatter light. The term "cross-section" refers to the intersection of a body in 2-dimensional space with a line, or of a body in 3-dimensional space with a plane. Preferably, cross-section refers to the intersection of a body in 3-dimensional space with a plane.

In a further example, the two classes of droplets have different diameters. All droplets in the microfluidic device within the ROI are detected using the previously specified droplet detection algorithm. The droplets are further classified as species A or species B depending on the droplet area. The droplet pairing ratio is measured by counting the number of species A droplets that are found upstream of each species B droplet. Species A has a smaller droplet diameter and travels faster than species B. Only the upstream Species A droplets will merge with downstream Species B droplets due to the differences in velocity. The species A droplets corresponding to a species B droplet at the inlet of the microfluidic channel are not counted in the droplet pairing measurement as it is not possible to detect and classify the off image-frame upstream droplet to get an exact pairing ratio for that species A: species B droplet set.

Figure 4:
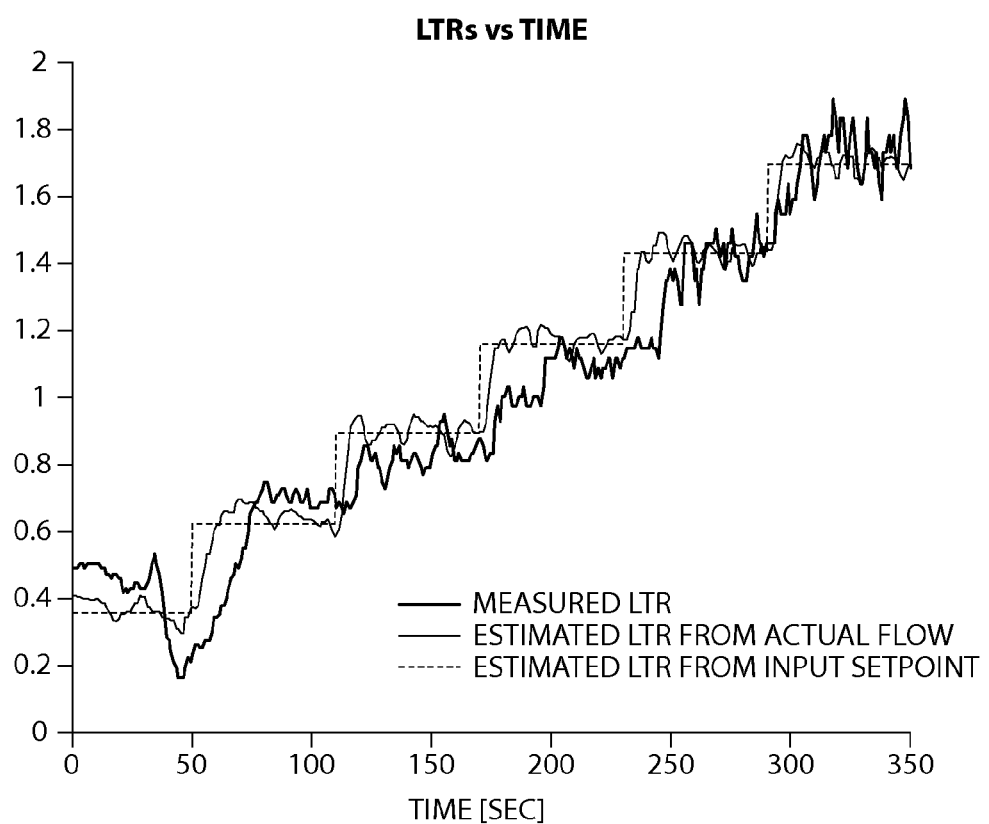
FIG. 4 is a graph of the Library to Template Ratio (LTR), also referred to as the droplet pairing ratio, versus time, showing that the droplet pairing ratio is well controlled over a range from 0.4 to 1.75 by adjusting the carrier fluid flow rates.
Figure 5A:
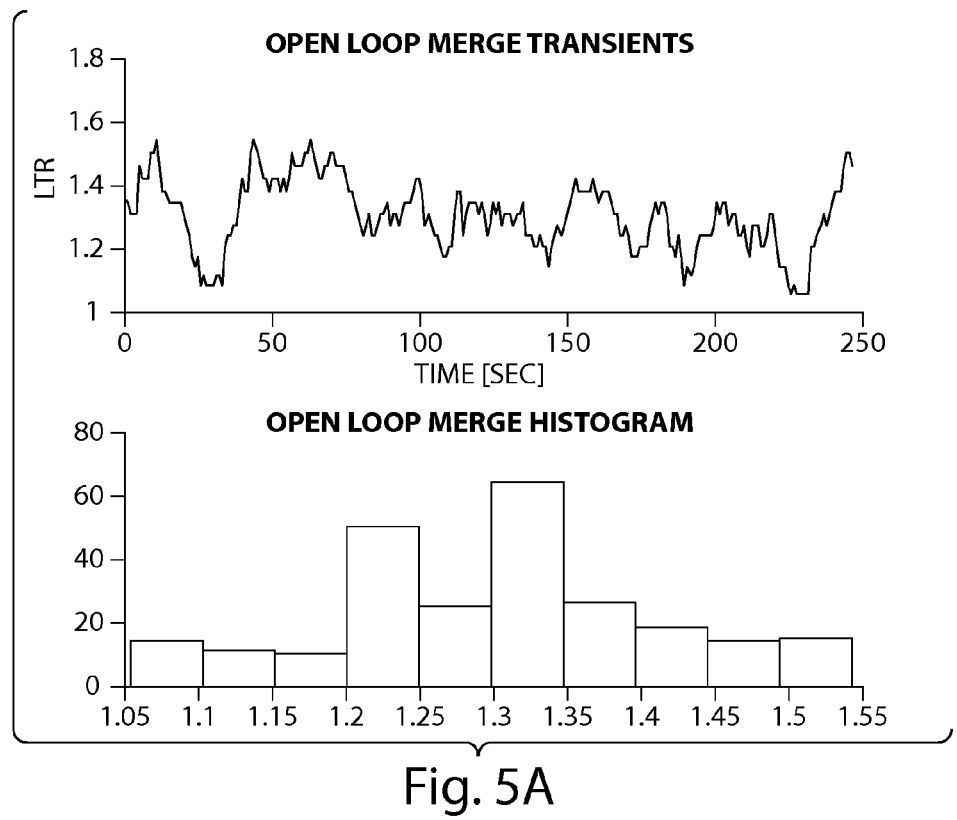
FIG. 5A is a pair of graphs, a line graph and its corresponding histogram, of the relationship of the LTR for open loop operation (with a rather large CV of 8.5%) versus time, showing that the output, or LTR, is not centered about the set point of 1.
Figure 5B:
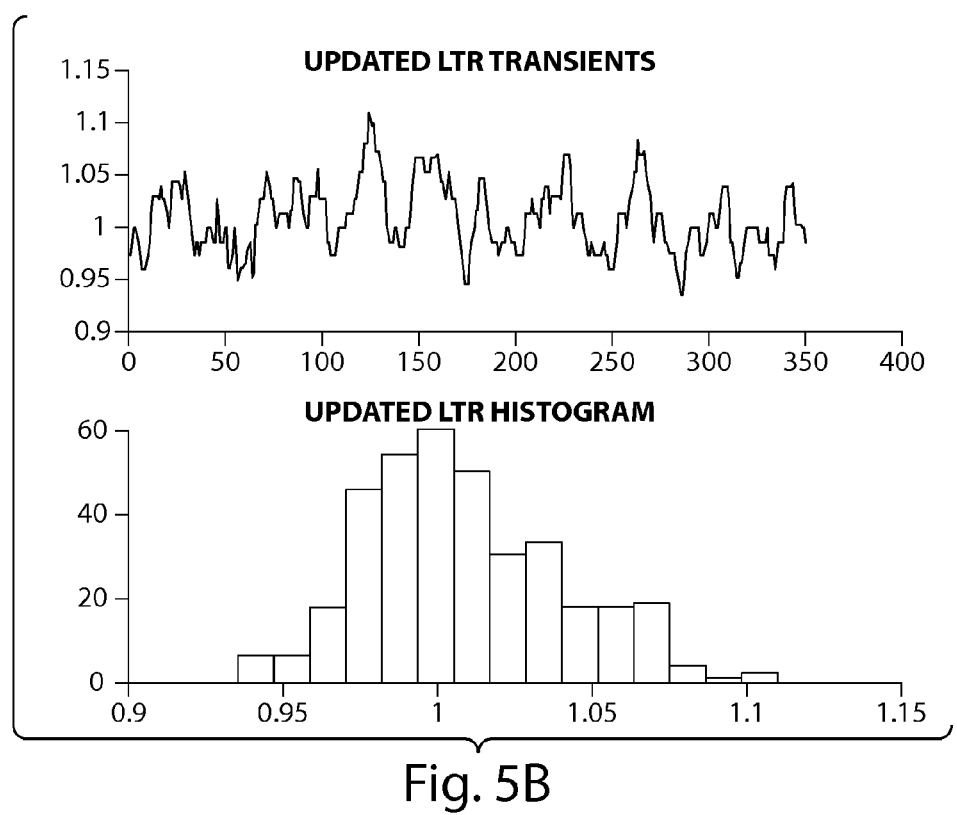
FIG. 5B is a pair of graphs, a line graph and its corresponding histogram, of the relationship of LTR for closed loop feedback (with a CV of 3.0%) versus time, showing that the output, or LTR, is centered about the set point of 1.

As shown in FIG. 4, the droplet pairing ratio (also referred to as Library to Template Ratio [LTR]) is well controlled over a range from 0.4 to 1.75 by adjusting the carrier fluid flow rates. FIG. 5a shows the LTR for open loop operation with a rather large CV (Coefficient of Variation (i.e., Standard Deviation/Mean)) of 8.5% and isn't centered about the set point of 1. FIG. 5b shows the results of applying closed loop feedback on the LTR, the output is centered on the set point of 1 and has a CV of 3%.

The invention provides a f feedback control system for independently controlling microfluidic droplet volume and frequency comprising: (a) providing a microfluidic system comprising at least one microfluidic channel; (b) producing a plurality of fluidic droplets within a carrier fluid within said microfluidic channel using a drive fluid; (c) assessing the frequency, volume, and flow rate of said plurality of droplets using an image sensor; (d) transmitting said assessed frequencies, volumes, and flow rates of the plurality of droplets from said image sensor to a feedback controller; (e) adjusting a flow rate of the carrier fluid using said feedback controller to attain a predetermined droplet frequency set point; and (f) adjusting a flow rate of the drive fluid using said feedback controller to attain a predetermined droplet volume set point; wherein said feedback control system independently determines and controls microfluidic droplet frequency and volume.

Droplet volume and frequency are intrinsically linked through the law of mass conservation; droplet frequency multiplied by droplet volume is the droplet volumetric flow rate. Neglecting any system losses such as leaks, the droplet volumetric flow rate is determined by the drive pump flow rate. The droplet frequency is a function of many factors such as the microfluidic nozzle geometry, carrier fluid flow rate, fluidic shear forces, viscosity, and surface tension and will thusly be different for different fluids even when operating under the same pump flow rates. Typically the fluidic system will be initialized with empirically found pump flow rates starting the system near the desired frequency rate and droplet volume set point. The first stage of control then starts to adjust the carrier-pump flow rate to move the droplet frequency towards the desired set point. Droplet frequency and volume are highly non-linear as a function of carrier flow rate, but in general, increasing the carrier flow rate will increase the droplet frequency and decrease droplet volume. Decreasing the carrier flow rate decreases the droplet frequency and increases the droplet volume. Once the droplet frequency has settled the second stage of control then adjusts the flow rate to manipulate the droplet volume towards the desired set point. Preferably, the second stage of control adjusts the drive pump flow rate and the resultant drive fluid.

The measurement of absolute droplet volume is of fundamental importance, but traditional methods of measurement require specialized skills in the art and relatively expensive optical instruments. These methods include fluorescence burst analysis and image analysis of projected droplet area, where the latter requires independent calibration most often achieved by the former method. Methods of the invention are easy to use, amenable to automation, and inexpensive to implement. This method can be used in conjunction with the imaging-based control feedback described above to create steady streams of droplets of known absolute size and frequency. The traditional methods are described first, below.

The most accessible measurement related to droplet volume is the volumetric flow rate, Q, of the sample fluid, that is, the liquid phase that forms the droplets and as opposed to the carrier fluid that surrounds the droplets. Typical microfluidic flow rates between 10 to $10^4$ μL/hr can be measured by numerous methods including piston displacement and heat transfer. Thus, all that remains to determine the average droplet volume is to measure the droplet frequency, v, because the average droplet volume, $\bar{V}$, equals $$\bar{V} = \frac{Q}{v}.$$

This commonly used relationship yields an average droplet size because the droplet frequency is determined over an ensemble of droplets.

Droplet frequency poses a more significant measurement challenge. Frequencies often reach ~10 kHz, requiring a measurement system with a very fast time response. Laser-induced fluorescence is the most common method, taking advantage of the high speed of low light detectors such as PMTs. In this method, droplets containing fluorophores emit a steady train of fluorescence bursts that is readily translated into droplet frequency by standard Fourier analysis. While quite robust, this approach requires familiarity with laser alignment inside a microscope and it also requires both expensive fluorescence excitation and detection. Methods of the invention eliminate both of these requirements.

The invention provides a method called Pulsed Illumination Scanning (PILS). The PILS method is a variant of conventional particle image velocimetry (PIV) that has been optimized for steady streams of regularly spaced droplets. Both approaches measure velocity by monitoring particle/droplet displacement in between successive images separated by a delay time, ΔT. As an example, in PIV the cross-correlation of two successive images of a field of randomly dispersed particles yields a singular peak corresponding to the uniform displacement of all of the particles in the field of view. However, cross-correlation of successive images of regularly spaced droplets yields a repeating set of peaks because each individual image has a high degree of autocorrelation. That is, except at the shortest delays between images, it is very difficult to deduce a priori which droplets correspond to each other. At very short delays, the percent uncertainty in the displacement measurement is unacceptably high for most applications.

In the PILS method, pairs of successive images are recorded with an increasing delay in time between images (increasing ΔT). The initial ΔT must be significantly shorter than the droplet period (the time between droplet arrivals, or 1/v) to avoid ambiguity in droplet associations between images. ΔT is then increased gradually to reduce the percent error in the displacement measurement, but without losing track of droplet associations. In fact, ΔT can even significantly exceed the droplet period so long as the association is maintained. In this manner, the PILS method overcomes the shortcomings of PIV by using both short delays to establish associations and long delays to reduce experimental error. However, manually stepping between delays can be quite tedious, so a specific PILS method based on Fourier analysis, called fPILS is provided herein, fPILS is readily automated.

Figure 9A:
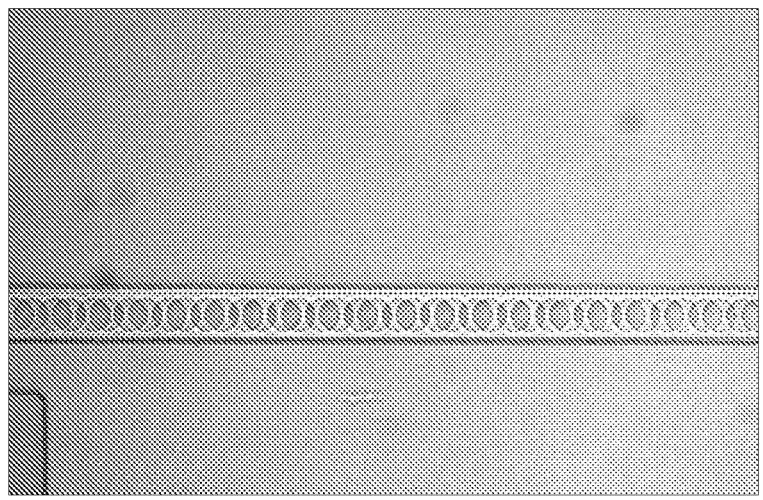
FIG. 9A a line-cut along the droplet train of a microfluidic channel.
Figure 9B:
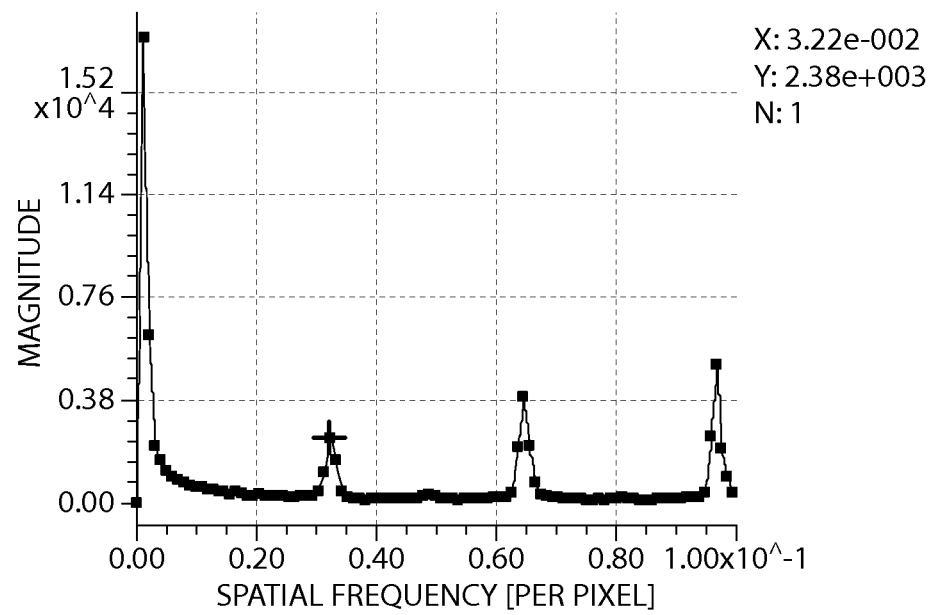
FIG. 9B is a one-dimensional Fourier transform of a line-cut along the droplet train (line cut in FIG. 9A) revealing the fundamental droplet frequency (spatial frequency) and its higher order harmonics.
Figure 9C:
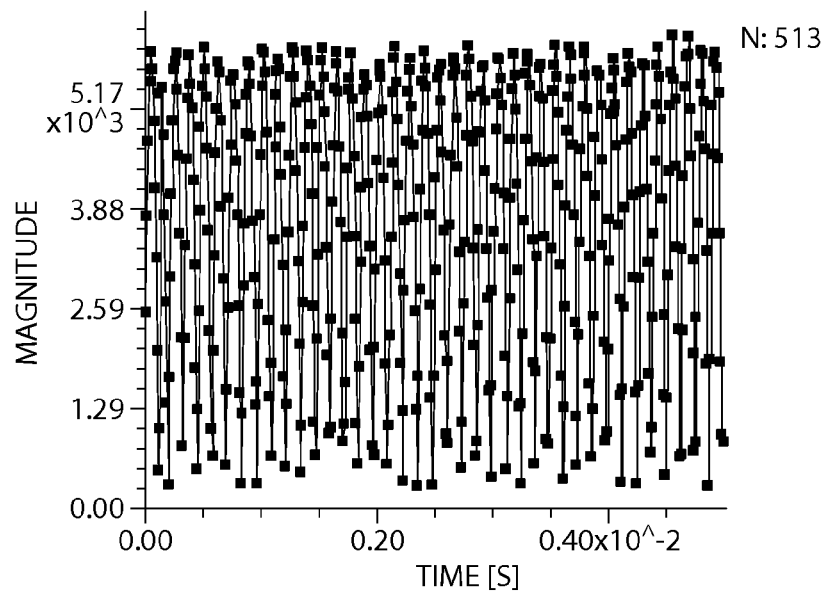
FIG. 9C is the amplitude of the fundamental frequency after each increase in the change in time, ΔT in multiple illumination images.
Figure 9D:
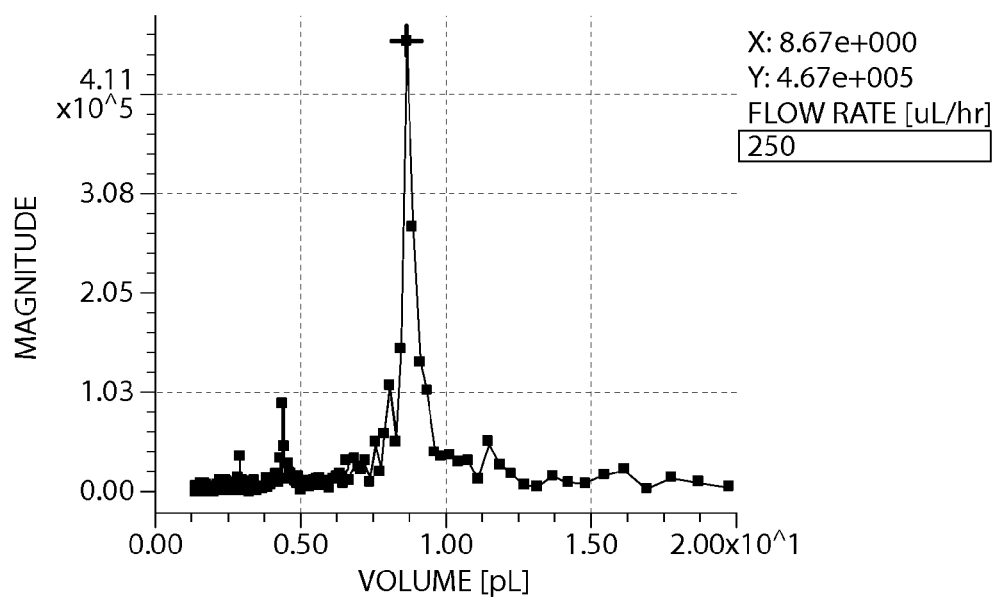
FIG. 9D is a second Fourier transform of the dependence of the fundamental frequency on ΔT revealing the desired temporal frequency of the droplets as a single pronounced peak.

In the first step of the fPILS method, a one-dimensional Fourier transform of a line-cut along the droplet train (line cut in FIG. 9A) reveals the fundamental droplet frequency (spatial frequency) and its higher order harmonics (FIG. 9B). The fundamental spatial frequency can be identified from a single image, but subsequent analysis requires both images separated by ΔT to be superimposed. A convenient and inexpensive method of superimposing images used here employs short pulses of illumination from an LED and an extended camera exposure that catches both pulses. The amplitude of the fundamental frequency is then monitored after each increase in ΔT (FIG. 9C) in the multiple illumination images. The amplitude of the fundamental spatial frequency oscillates with a period equal to the droplet period. This can be understood by considering the case when ΔT equals half the droplet period. In this case, the droplets in the second exposure appear halfway in between the droplets from the first exposure. In effect, the superimposed image looks like the droplets have exactly doubled their frequency. The new fundamental spatial frequency is now twice the original, and the amplitude of the original frequency is ideally zero. Thus the amplitude of the fundamental spatial frequency oscillates between a maximum at overlap of droplets and a minimum at ½ offset between droplets with a period equal to the droplet period. A second Fourier transform of the dependence of the fundamental frequency on ΔT reveals the desired temporal frequency of the droplets as a single pronounced peak (FIG. 9D).

The fPILS method is low cost, robust, precise, and accurate. The method only requires an inexpensive camera that is standard equipment on any droplet characterization platform, a very inexpensive LED, and a simple pulsed current source to power the LED. The LED pulser used here was based on the common and inexpensive PIC microcontroller. The method is also extremely robust against drift in microscope focus because it is based on the repetition of features within an image. Even quite out-of-focus images show excellent repetition. The resolution of the measurement rivals alternative approaches when many periods of the oscillation in fundamental spatial frequency are observed. In fact, at the longest ΔT's in FIG. 9C the droplets in the first image have completely displaced outside of the field of view in the second image. Such extended ΔT's are impossible with conventional PIV, highlighting the extra information accessible from a repetitive system. The accuracy of the method is dependent on the uncertainty in ΔT and Q. Typically ΔT is very well known, originating from an extremely accurate and precise crystal oscillator. Thus, the overall uncertainly in the measurement is most likely dominated by the error in Q.

Figure 6:
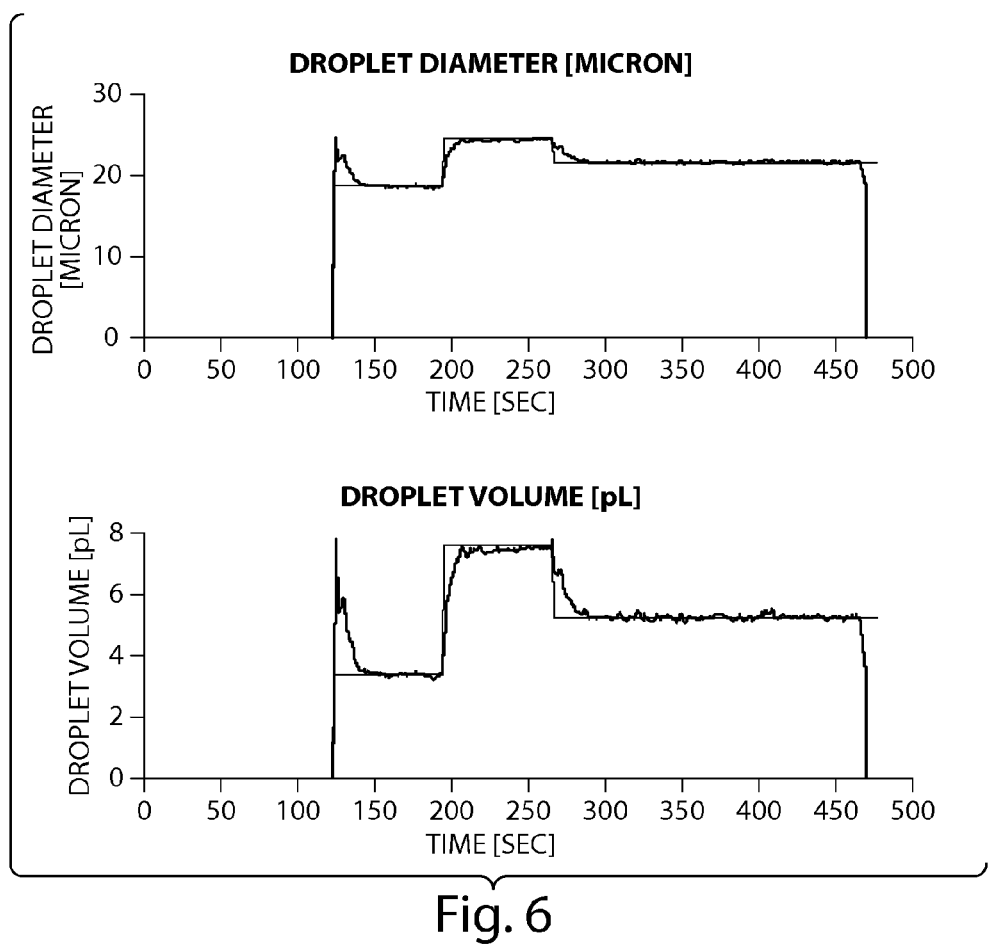
FIG. 6 is a pair of graphs of droplet diameter (top) or droplet volume (bottom) versus time, demonstrating the droplet volume control step response. Green or Straight Line=set point. Blue or Jagged Line=measured output.
Figure 7:
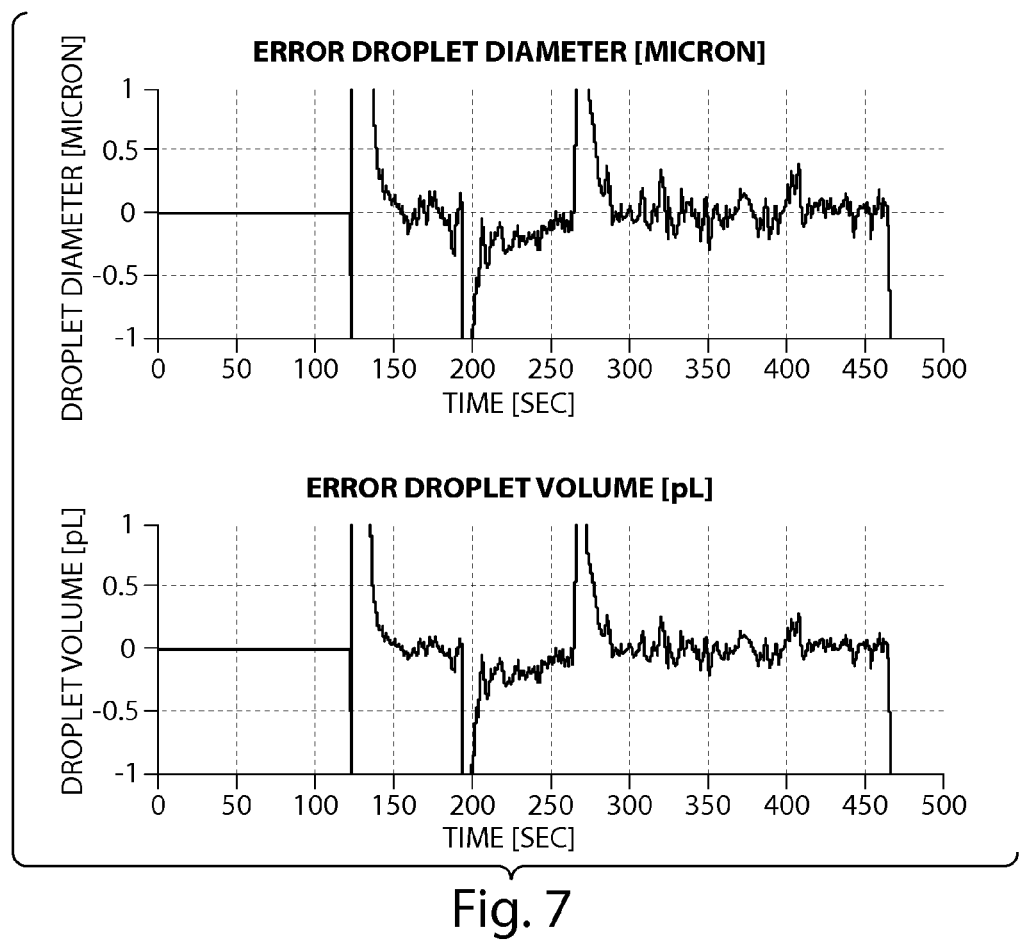
FIG. 7 is a pair of graphs of droplet diameter (top) or droplet volume (bottom) versus time, demonstrating that error in the droplet volume is minimal, i.e. below 0.5 pL.

An example of droplet volume control is shown in FIG. 6. The droplet volume is detected using either fPILS or inferred from the droplet projected area as detailed in the droplet detection section. The drive fluid is then automatically adjusted using PID control to control the droplet volume. It can be seen that droplet diameter and droplet volume are quite controllable and settle to the desired set point in under 20 seconds. FIG. 7 shows the error in the droplet volume is quite low, well below 0.5 pL.

Similarly to droplet volume control, above, the droplet frequency can be controlled in a straightforward manner. The droplet frequency can be measured directly by the fPILS method, fluorescence burst analysis, or any other method. Comparison of the measured frequency with the target set point yields an error signal that can be fed back to a standard controller, such as a PID controller. In the preferred control scheme, the carrier flow rate is increased to increase the droplet frequency, and vice versa. Any other method of adjusting the droplet frequency can also be used.

Figure 8:
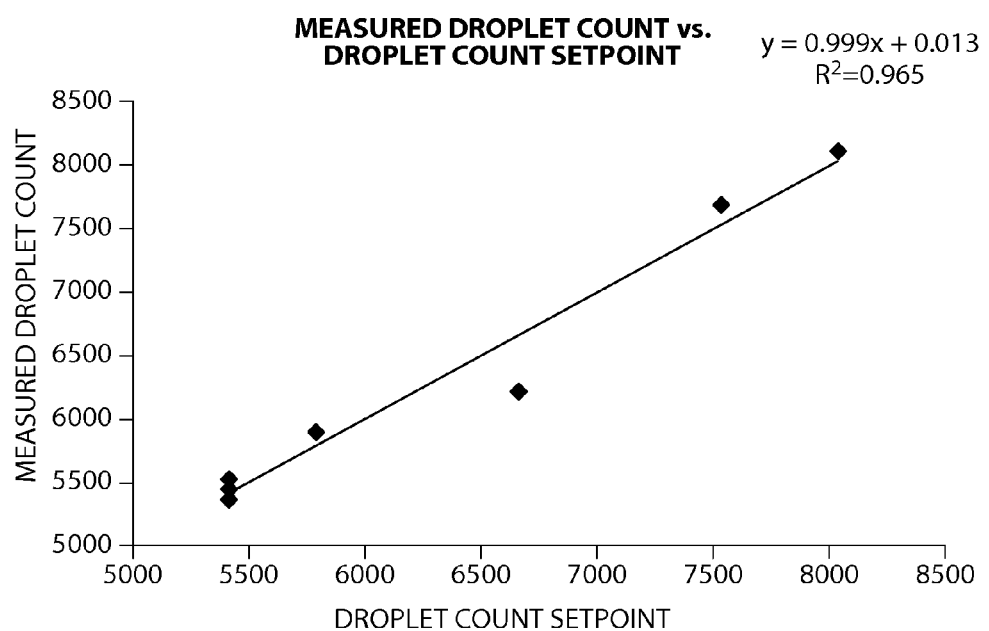
FIG. 8 is a graph of the measured droplet count vs. droplet count set point, demonstrating droplet count control.

An example of droplet count control is shown in FIG. 8. The current total droplet count is detected by integrating the fPILS algorithm output over time or by integrating the droplet count per image frame over time. Once the desired number of droplets has been detected, all plump flow stops, thus stopping droplet formation/release. It can be seen that the droplet release/generation count is quite controllable over a large range and is highly linear.

This present invention provides various methods of droplet detection and analysis.

"Droplet detection" refers to the identification and selection of droplets through an automatic process. In one example, droplet detection includes the steps of image acquisition, intensity thresholding, area thresholding, circularity filtering and accumulating the filtered results. The term "image acquisition" refers to acquiring images of droplets. In a preferred aspect of this method, images of droplets are acquired in a microfluidic device. In another preferred aspect of this method, images of droplets are acquired in the region of interest (ROI). As used herein, "region of interest" or "ROI" refers to locations in the microfluidic device where certain behaviors of droplets (e.g., pairing, merging, combination, etc.) occur or where certain actions (e.g., electrification, mechanical deformation, etc.) are applied to droplets. Preferably, the region of interest or ROI has two ends wherein one end is at the location where droplets enter the ROI and the other end is at the location where droplets exit the ROI. In a preferred example, the ROI is where pairing of droplets occurs. In another preferred example, the ROI is where combination of droplets occurs.

Image acquisition is performed using a device with means to capture images at a sufficient acquisition rate (e.g., 10 images per second) and exposure time (between 1-10 μs, preferably 5 μs). Alternatively, or in addition, images are acquired with a digital device (e.g., digital camera). The composition of the droplets has a different refractive index from that of the surrounding carrier fluid. Thus, due to refraction, the boundary of the droplet has a different brightness, e.g., the boundary of the droplet is darker. Therefore, the corresponding pixels in the image have different values from those of the surrounding pixels.

One method of droplet detection is machine vision. One of ordinary skill in the art of machine vision knows that each image must have sufficient contrast, focus and resolution to have a robust detection method. Thus, adjusting the optics, illumination and focus to obtain a suitable image is imperative for droplet detection. The term "accumulated contour detection" refers to the process in which droplets are detected and characterized through multiple image processing filters as follows:

1. "Intensity threshold" the image at threshold t. In one example t is initialized to the minimum image intensity value.
2. Detect all contours in the threshold image ("contour detection").
3. Filter contours based on "area thresholding."
4. Filter contours based on "circularity thresholding."
5. Filter contours based on spatial location within the image.
6. Accumulate contours into the "contour accumulator image." For example, in FIG. 1, an image of droplets in the ROI shows droplets of two sizes (top panel). The bottom panel shows the final "contour accumulator image" where grey level intensity corresponds to the number of times each pixel was added to the accumulator image. All other pixels were assigned the value "0", shown as black.

7. Increment the threshold value t.
8. Repeat steps 1 though 7 until t reaches the maximum image intensity value.
9. "Intensity threshold" the "contour accumulator image" to select only droplets with a significant number of votes.

The term "intensity thresholding" refers to the process where the value of each pixel in an image is compared with a preset value called "threshold value", and pixels that have a value lower than the threshold value are assigned a designated value, e.g., 0, and pixels that have a higher value are assigned another designated value, e.g., 1. The output is called a binary threshold image.

The term "contour detection" refers to the process where the perimeter of connected non-zero pixels is detected. Connectivity defines which pixels are connected to other pixels. A set of pixels in a binary threshold image that form a connected group is referred to as an "object" and the perimeter of the "object" is referred to as a "contour".

The term "area thresholding" refers to the process where the number of pixels in an area confined by a "contour" is calculated and compared with a set of preset values, and, according to the result from the comparison, all pixels included in the area are assigned to designated values, e.g., 0 and 1. In one example, areas with the number of pixels either smaller than a preset value $t_1$ or bigger than a preset value $t_2$ are assigned a designated value, e.g., 0, to all their pixels, and areas with the number of pixels no smaller than $t_1$ and no bigger than $t_2$ are assigned a designated value, e.g., 1, to all their pixels. Area thresholding detects droplets of sizes within a given range The term "circularity filtering" refers to the process where formula I is applied to an area confined by a contour and the resulting value Circ is compared with a preset range of values. Only those areas with a Circ value within the given range are selected. For droplets that are spherical, and, thus, have a circular cross-section, circularity filtering removes contaminants which often have irregular shapes. In formula I, Area and perimeter refer to the total number of pixels included in the area and the total number of pixels present on the boundary of the area, respectively.

$$Circ = \frac{4\pi \cdot \text{Area}}{perimeter^2} \quad (I)$$

The term "contour accumulation" refers to the process where the results of intensity thresholding, contour detection, area thresholding and circularity filtering are summed into an "accumulator image". The "accumulator image" keeps count of the number of times each pixel passes the applied filters. Only pixels that pass the filters many times are actually droplets; this reduces spurious results from illumination variations and digital sensor noise.

Figure 2:
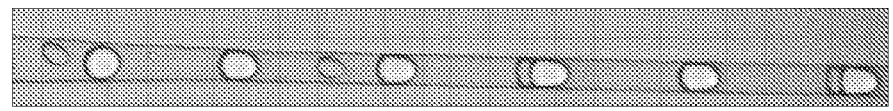
FIG. 2 is a photograph of an image of microdroplets shown in cross-section, in which the droplets of bigger cross-sectional area were pseudo-colored yellow (light shaded droplets) and the droplets of smaller cross-sectional area were pseudo-colored blue (dark shaded droplets).

The term "Droplet classification" refers to the process where droplets are classified according to their specific properties. Such properties include, but are not limited to, size (e.g., diameter, perimeter, diagonal, volume, area of cross-section, moments of inertia, etc.), shape (e.g., spherical, elliptical, rectangular, etc.), color, refractive index and extinction coefficient. In one example, the droplets are classified according to the area of their cross-section. For example, in FIG. 2, cross-sections of droplets are shown, and the droplets of bigger cross-section area were automatically colored yellow (light shaded) and the droplets of smaller cross-section area were colored blue (dark shaded).

Figure 10:
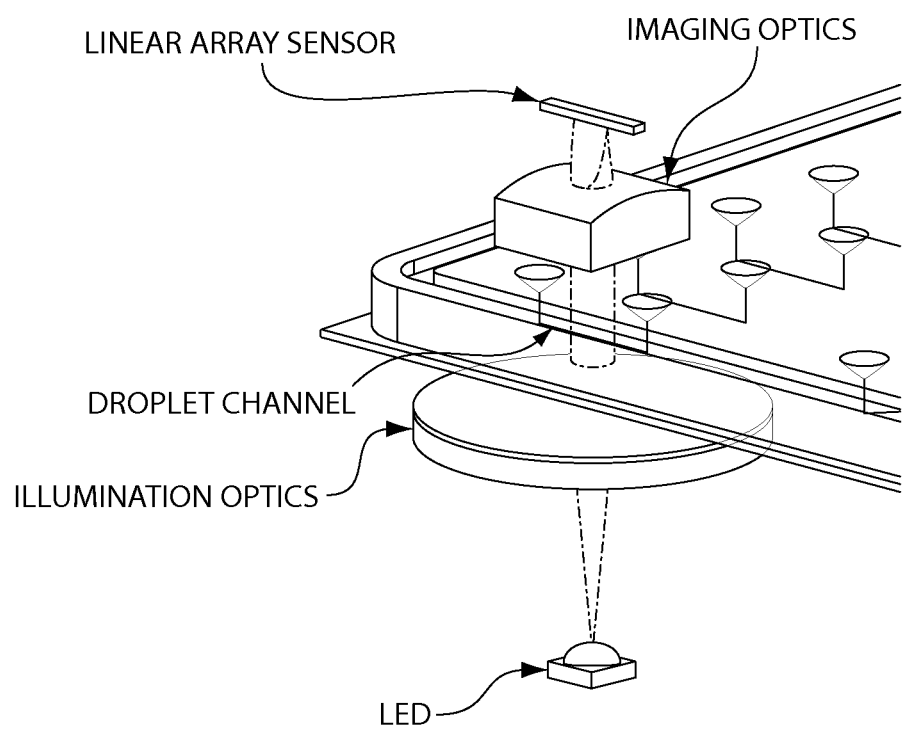
FIG. 10 is an illustration of a trans-illumination scheme.

The invention provides a method to measure every single droplet at nominal generation rates (typically 1 kHz to 10 kHz). Real-time measurement of droplet frequency, droplet spacing, effective droplet diameter, droplet count and nominal bulk fluid flow rates are easily detected. FIG. 10, shows a trans-illumination scheme but the invention can also include any illumination scheme, including but not limited to, epi-illumination and dark-field illumination schemes. The invention includes a light source, illumination optics, imaging optics and a linear sensor array. The light source can include any light source, including but not limited to, LED, laser, incandescent light bulb, fiber optic bundle, and OLED. Preferably, the light source is an LED. The illumination optics can include any illumination optics, including but not limited to, fiber optics, GRIN lens, multiple element lens and light shaping diffusers. A preferred embodiment is a single plano-convex lens positioned such that the LED is imaged at infinity. There may be an aperture to control the illuminated field-of-view to illuminate only the area near the microfluidic channel. The imaging optics can include any imaging optics, including but not limited to, cylindrical lens, fiber optics, GRIN lens, anamorphic lenses, and multiple element lenses. A preferred embodiment is a cylindrical lens which images a 2D area from the microfluidic device onto a single line of the linear array sensor. There may be an aperture to control optical aberrations and stray light. The linear sensor array can be any linear sensor array. A preferred embodiment is a high speed (>8 MHz) linear array sensor with at least 128 pixels and 5 µm pixel size.

Figure 11:
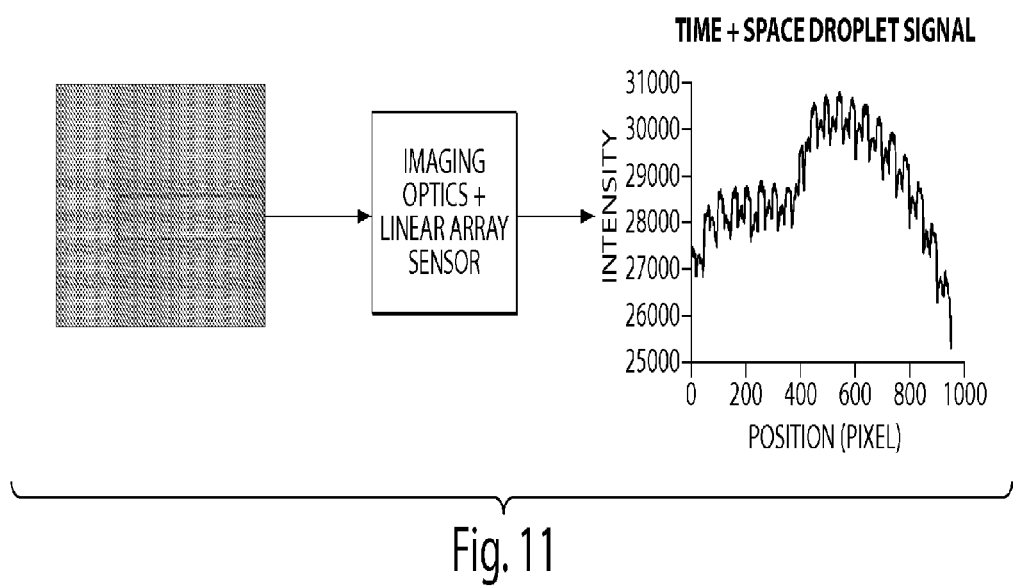
FIG. 11 is a graph showing that the imaging optics "squeezes" a 2D image into a 1D image by optically summing what would be the columns of the blue region of interest into a single line.

In this method, the imaging optics "squeezes" a 2D image into a 1D image by optically summing what would be the columns of the blue region of interest into a single line as shown in FIG. 11. High-speed linear array sensors with 8 MHz and faster readout rates which provide an inexpensive replacement for the area-scan CCD imager are readily available. The high readout rate and linear pixel spacing allows the measurement of droplet parameters with very high precision in time and space respectively.

Figure 12:
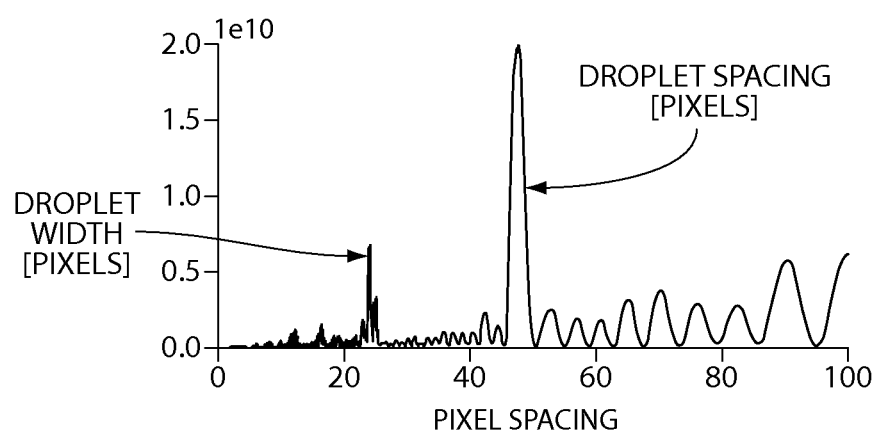
FIG. 12 is a graph showing that the average droplet spacing is approximately 50 pixels and droplet diameter is approximately 25 pixels.

A single image from the linear sensor array allows the measurement of droplet spacing and droplet diameter. As described above and shown in FIG. 11, the output of the linear sensor array clearly shows a periodic signal representing the droplets as they are positioned within the microfluidic channel. Droplet position measured in pixels can be converted to physical position by determining the optical magnification of the imaging optics. There are many ways to analyze period signals but in one embodiment measurement is as follows: (1) compute the Fourier Transform of the 1D image; (2) search for the maximum power signal from the transformed data; (3) the droplet spacing corresponds to the transformed data with maximum power signal. FIG. 12 shows that the average droplet spacing is approximately 50 pixels and droplet diameter is approximately 25 pixels.

Taking many samples over time from the linear sensor array allows the measurement of droplet frequency, droplet count and bulk fluid flow rate. Droplet frequency can be computed by applying the Fourier Transform to the time data in a similar manner to the analysis performed on the spatial data described previously. Typical linear sensor arrays have readout rates at 8 MHz and above, this easily allows the measurement of each droplet at typical droplet generation rates of up to 10 KHz. The droplet count is determined by integrating the droplet frequency with respect to time. The bulk fluid flow rate is the product of the microfluidic channel cross-sectional area, droplet frequency and droplet spacing.

The combination of image processing and feedback control provide other functionality beyond droplet control. The inherent stability and known reference allows for the use of these components to identify and diagnose issues in the system. The system can be tuned to be robust to run-to-run and intra-run changes in fluid environment, pump controls, and microfluidic device variations. The inherent stability present in this system that is not present in an uncontrolled system, can be used to identify system issues or instabilities. Intra- and inter-run patterns can be used to detect fluidic leaks, restrictions, mechanical issues, and input conditions.

Another secondary byproduct of image processing is the examination of droplets by size across periods of time (i.e., an entire run). By creating a histogram of droplets, a new diagnostic tool was made available. Beyond verification of the feedback control operation, these histograms can identify issues in pre-emulsified library, fluidic interference in the chip, and other system issues.

The present invention also provides a Background Subtraction Algorithm. This method provides improvements over the accumulating contour detection method. Specifically, the Background Subtraction Algorithm improves CPU utilization as this method is less computer intensive. It prevents or decreases sensitivity to variations in illumination and focus quality, when measuring a certain parameter of the detected droplet (like size). Moreover, it prevents or decreases noise amplification when measuring a certain parameter of the detected droplet (like size), due to accumulation of contours of the same droplet. Specifically the Background Subtraction Algorithm is fast, produces less measurement noise and with improved optics, it is possible to use single threshold to detect contours.

Specifically, the Background Subtraction Algorithm takes advantages of the fact that droplets always appear to be moving, it calculates image difference of every two consecutive images. If the absolute value of the maximum difference between images is less then Threshold1, then one of the images is selected and saved as a current background image. This is an image of the channel without droplets. Once background image is obtained each new image is also differenced against the current background image and Threshold2 is applied to the difference image. Contours are then obtained from the binary image and filtered using same circularity, size and position filters described for Contour Accumulation Algorithm. Advantage of the subtraction is that it allows to remove image of the droplet channel that can make it harder to detect outer contour of the droplet which is less prone to size variations due to illumination non-uniformity and defocusing.

A microfluidic system of the present invention includes one or more microfluidic channels. The terms microfluidic system, microfluidic device, microsubstrate, substrate, microchip, and chip are used interchangeably herein. The microfluidic system can include at least one inlet channel, at least one main channel and at least one inlet module. The microfluidic system can further include at least one coalescence module, at least one detection module and one or more sorting modules. The sorting module can be in fluid communication with branch channels which are in fluid communication with one or more outlet modules (collection module or waste module). For sorting applications, at least one detection module cooperates with at least one sorting module to divert flow via a detector-originated signal. It shall be appreciated that the "modules" and "channels" are in fluid communication with each other and therefore may overlap; i.e., there may be no clear boundary where a module or channel begins or ends. The dimensions of the substrate are those of typical microchips, ranging between about 0.5 cm to about 15 cm per side and about 1 micron to about 1 cm in thickness. The microfluidic and specific modules are described in further detail in WO 2006/040551; WO 2006/040554; WO 2004/002627; WO 2004/091763; WO 2005/021151; WO 2006/096571; WO 2007/089541; WO 2007/081385 and WO 2008/063227, each of which is incorporated by reference in its entirety.

The microfluidic substrates of the present invention include channels that form the boundary for a fluid. A "channel," as used herein, means a feature on or in a substrate that at least partially directs the flow of a fluid. In some cases, the channel may be formed, at least in part, by a single component, e.g., an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel). In embodiments where the channel is completely covered, at least one portion of the channel can have a cross-section that is completely enclosed, and/or the entire channel may be completely enclosed along its entire length with the exception of its inlet and outlet.

The channels of the invention can be formed, for example by etching a silicon chip using conventional photolithography techniques, or using a micromachining technology called "soft lithography" as described by Whitesides and Xia, Angewandte Chemie International Edition 37, 550 (1998).

An open channel generally will include characteristics that facilitate control over fluid transport, e.g., structural characteristics (an elongated indentation) and/or physical or chemical characteristics (hydrophobicity vs. hydrophilicity) and/or other characteristics that can exert a force (e.g., a containing force) on a fluid. The fluid within the channel may partially or completely fill the channel. In some cases the fluid may be held or confined within the channel or a portion of the channel in some fashion, for example, using surface tension (e.g., such that the fluid is held within the channel within a meniscus, such as a concave or convex meniscus). In an article or substrate, some (or all) of the channels may be of a particular size or less, for example, having a largest dimension perpendicular to fluid flow of less than about 5 mm, less than about 2 mm, less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100nm, less than about 30 nm, or less than about 10 nm or less in some cases.

A "main channel" is a channel of the device of the invention which permits the flow of molecules, cells, small molecules or particles past a coalescence module for coalescing one or more droplets, and, if present, a detection module for detection (identification) or measurement of a droplet and a sorting module for sorting a droplet based on the detection in the detection module. The main channel is typically in fluid communication with the coalescence, detection and/or sorting modules, as well as, an inlet channel of the inlet module. The main channel is also typically in fluid communication with an outlet module and optionally with branch channels, each of which may have a collection module or waste module. These channels permit the flow of molecules, cells, small molecules or particles out of the main channel. An "inlet channel" permits the flow of molecules, cells, small molecules or particles into the main channel. One or more inlet channels communicate with one or more means for introducing a sample into the device of the present invention. The inlet channel communicates with the main channel at an inlet module.

The microfluidic substrate can also comprise one or more fluid channels to inject or remove fluid in between droplets in a droplet stream for the purpose of changing the spacing between droplets.

The channels of the device of the present invention can be of any geometry as described. However, the channels of the device can comprise a specific geometry such that the contents of the channel are manipulated, e.g., sorted, mixed, prevent clogging, etc.

A microfluidic substrate can also include a specific geometry designed in such a manner as to prevent the aggregation of biological/chemical material and keep the biological/chemical material separated from each other prior to encapsulation in droplets. The geometry of channel dimension can be changed to disturb the aggregates and break them apart by various methods, that can include, but is not limited to, geometric pinching (to force cells through a (or a series of) narrow region(s), whose dimension is smaller or comparable to the dimension of a single cell) or a barricade (place a series of barricades on the way of the moving cells to disturb the movement and break up the aggregates of cells).

To prevent material (e.g., cells and other particles or molecules) from adhering to the sides of the channels, the channels (and coverslip, if used) may have a coating which minimizes adhesion. The surface of the channels of the microfluidic device can be coated with any anti-wetting or blocking agent for the dispersed phase. The channel can be coated with any protein to prevent adhesion of the biological/chemical sample. Channels can be coated by any means known in the art. For example, the channels are coated with Teflon®, BSA, PEG-silane and/or fluorosilane in an amount sufficient to prevent attachment and prevent clogging. In another example, the channels can be coated with a cyclized transparent optical polymer obtained by copolymerization of perfluoro (alkenyl vinyl ethers), such as the type sold by Asahi Glass Co. under the trademark Cytop. In such an example, the coating is applied from a 0.1-0.5 wt % solution of Cytop CTL-809M in CT-Sole 180. This solution can be injected into the channels of a microfluidic device via a plastic syringe. The device can then be heated to about 90° C. for 2 hours, followed by heating at 200° C. for an additional 2 hours. In another embodiment, the channels can be coated with a hydrophobic coating of the type sold by PPG Industries, Inc. under the trademark Aquapel (e.g., perfluoroalkylalkylsilane surface treatment of plastic and coated plastic substrate surfaces in conjunction with the use of a silica primer layer) and disclosed in U.S. Pat. No. 5,523,162. By fluorinating the surfaces of the channels, the continuous phase preferentially wets the channels and allows for the stable generation and movement of droplets through the device. The low surface tension of the channel walls thereby minimizes the accumulation of channel clogging particulates.

The surface of the channels in the microfluidic device can be also fluorinated by any means known in the art to prevent undesired wetting behaviors. For example, a microfluidic device can be placed in a polycarbonate dessicator with an open bottle of (tridecafluoro-1,1,2,2-tetrahydrooctyl)trichlorosilane. The dessicator is evacuated for 5 minutes, and then sealed for 20-40 minutes. The dessicator is then backfilled with air and removed. This approach uses a simple diffusion mechanism to enable facile infiltration of channels of the microfluidic device with the fluorosilane and can be readily scaled up for simultaneous device fluorination.

The fluids described herein are related to the fluids within a microfluidic device and the fluids used to introduce microdroplets or other items into a microfluidic device.

The microfluidic device of the present invention is capable of controlling the direction and flow of fluids and entities within the device. The term "flow" means any movement of liquid or solid through a device or in a method of the invention, and encompasses without limitation any fluid stream, and any material moving with, within or against the stream, whether or not the material is carried by the stream. For example, the movement of molecules, beads, cells or virions through a device or in a method of the invention, e.g. through channels of a microfluidic chip of the invention, comprises a flow. This is so, according to the invention, whether or not the molecules, beads, cells or virions are carried by a stream of fluid also comprising a flow, or whether the molecules, cells or virions are caused to move by some other direct or indirect force or motivation, and whether or not the nature of any motivating force is known or understood. The application of any force may be used to provide a flow, including without limitation, pressure, capillary action, electro-osmosis, electrophoresis, dielectrophoresis, optical tweezers, and combinations thereof, without regard for any particular theory or mechanism of action, so long as molecules, cells or virions are directed for detection, measurement or sorting according to the invention. Specific flow forces are described in further detail herein.

The flow stream in the main channel is typically, but not necessarily, continuous and may be stopped and started, reversed or changed in speed. A liquid that does not contain sample molecules, cells or particles can be introduced into a sample inlet well or channel and directed through the inlet module, e.g., by capillary action, to hydrate and prepare the device for use. Likewise, buffer or oil can also be introduced into a main inlet region that communicates directly with the main channel to purge the device (e.g., or "dead" air) and prepare it for use. If desired, the pressure can be adjusted or equalized, for example, by adding buffer or oil to an outlet module.

As used herein, the term "fluid stream" or "fluidic stream" refers to the flow of a fluid, typically generally in a specific direction. The fluidic stream may be continuous and/or discontinuous. A "continuous" fluidic stream is a fluidic stream that is produced as a single entity, e. g., if a continuous fluidic stream is produced from a channel, the fluidic stream, after production, appears to be contiguous with the channel outlet. The continuous fluidic stream is also referred to as a continuous phase fluid or carrier fluid. The continuous fluidic stream may be laminar, or turbulent in some cases. The continuous phase fluid within the main channel of the microfluidic device is referred to as the carrier fluid. The continuous phase fluid outside the main channel of the microfluidic device which is used to introduce a sample fluid (either a continuous sample fluid or a discontinuous sample fluid (e.g., pre-made fluidic droplets) into the microfluidic device is referred to as the drive fluid.

Similarly, a "discontinuous" fluidic stream is a fluidic stream that is not produced as a single entity. The discontinuous fluidic stream is also referred to as the dispersed phase fluid or sample fluid. A discontinuous fluidic stream may have the appearance of individual droplets, optionally surrounded by a second fluid. The dispersed phase fluid can include a biological/chemical material. The biological/chemical material can be tissues, cells, particles, proteins, antibodies, amino acids, nucleotides, small molecules, and pharmaceuticals. The biological/chemical material can include one or more labels known in the art. The label can be an optical label, an enzymatic label or a radioactive label. The label can be any detectable label, e.g., a protein, a DNA tag, a dye, a quantum dot or a radio frequency identification tag, or combinations thereof. Preferably the label is an optical label. The label can be detected by any means known in the art. Preferably, the label is detected by fluorescence polarization, fluorescence intensity, fluorescence lifetime, fluorescence energy transfer, pH, ionic content, temperature or combinations thereof.

The term "emulsion" refers to a preparation of one liquid distributed in small globules (also referred to herein as drops, droplets or NanoReactors) in the body of a second liquid. For example, the discontinuous phase can be an aqueous solution and the continuous phase can a hydrophobic fluid such as an oil. This is termed a water in oil emulsion. Alternatively, the emulsion may be a oil in water emulsion. In that example, the continuous phase can be an aqueous solution and the discontinuous phase is a hydrophobic fluid, such as an oil (e.g., decane, tetradecane, or hexadecane). The droplets or globules of oil in an oil in water emulsion are also referred to herein as "micelles", whereas globules of water in a water in oil emulsion may be referred to as "reverse micelles".

The fluidic droplets may each be substantially the same shape and/or size. The droplets may be uniform in size. The shape and/or size can be determined, for example, by measuring the average diameter or other characteristic dimension of the droplets. The "average diameter" of a plurality or series of droplets is the arithmetic average of the average diameters of each of the droplets. Those of ordinary skill in the art will be able to determine the average diameter (or other characteristic dimension) of a plurality or series of droplets, for example, using laser light scattering, microscopic examination, or other known techniques. The diameter of a droplet, in a non-spherical droplet, is the mathematically-defined average diameter of the droplet, integrated across the entire surface. The average diameter of a droplet (and/or of a plurality or series of droplets) may be, for example, less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers in some cases. The average diameter may also be at least about 1 micrometer, at least about 2 micrometers, at least about 3 micrometers, at least about 5 micrometers, at least about 10 micrometers, at least about 15 micrometers, or at least about 20 micrometers in certain cases.

As used herein, the term "NanoReactor" and its plural encompass the terms "droplet", "nanodrop", "nanodroplet", "microdrop" or "microdroplet" as defined herein, as well as an integrated system for the manipulation and probing of droplets, as described in detail herein. Nanoreactors as described herein can be 0.1-1000 μm (e.g., 0.1, 0.2 . . . 5, 10, 15, 20, 25, 30, 35, 40, 45, 50 . . . 1000), or any size within this range. Droplets at these dimensions tend to conform to the size and shape of the channels, while maintaining their respective volumes. Thus, as droplets move from a wider channel to a narrower channel they become longer and thinner, and vice versa.

The microfluidic substrate of this invention most preferably generate round, highly uniform, monodisperse droplets (<1.5% polydispersity). Droplets and methods of forming monodisperse droplets in microfluidic channels is described in WO 2006/040551; WO 2006/040554; WO 2004/002627; WO 2004/091763; WO 2005/021151; WO 2006/096571; WO 2007/089541; WO 2007/081385 and WO 2008/063227.

The droplet forming liquid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with the population of molecules, cells or particles to be analyzed and/or sorted can be used. The fluid passing through the main channel and in which the droplets are formed is one that is immiscible with the droplet forming fluid. The fluid passing through the main channel can be a non-polar solvent, decane (e.g., tetradecane or hexadecane), fluorocarbon oil, silicone oil or another oil (for example, mineral oil).

The droplet may also contain biological/chemical material (e.g., molecules, cells, or other particles) for combination, analysis and/or sorting in the device. The droplets of the dispersed phase fluid can contain more than one particle or can contain no more than one particle.

Droplets of a sample fluid can be formed within the inlet module on the microfluidic device or droplets (or droplet libraries) can be formed before the sample fluid is introduced to the microfluidic device ("off chip" droplet formation). To permit effective interdigitation, coalescence and detection, the droplets comprising each sample to be analyzed must be monodisperse. As described in more detail herein, in many applications, different samples to be analyzed are contained within droplets of different sizes. Droplet size must be highly controlled to ensure that droplets containing the correct contents for analysis and coalesced properly. As such, the present invention provides devices and methods for forming droplets and droplet libraries.

The fluids used in the invention may contain one or more additives, such as agents which reduce surface tensions (surfactants). Surfactants can include Tween, Span, fluorosurfactants, and other agents that are soluble in oil relative to water. In some applications, performance is improved by adding a second surfactant to the aqueous phase. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing. The present invention provides compositions and methods to stabilize aqueous droplets in a fluorinated oil and minimize the transport of positively charged reagents (particularly, fluorescent dyes) from the aqueous phase to the oil phase.

The droplets may be coated with a surfactant. Preferred surfactants that may be added to the continuous phase fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglycerl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates). In addition, ionic surfactants such as sodium dodecyl sulfate (SDS) may also be used. However, such surfactants are generally less preferably for many embodiments of the invention. For instance, in those embodiments where aqueous droplets are used as nanoreactors for chemical reactions (including biochemical reactions) or are used to analyze and/or sort biomaterials, a water soluble surfactant such as SDS may denature or inactivate the contents of the droplet.

The continuous phase fluid (carrier fluid and the drive fluid) can be an oil (e.g., decane, tetradecane or hexadecane) or fluorocarbon oil that contains a surfactant (e.g., a non-ionic surfactant such as a Span surfactant) as an additive (preferably between about 0.2 and 5% by volume, more preferably about 2%). A user can preferably cause the carrier fluid to flow through channels of the microfluidic device so that the surfactant in the carrier fluid coats the channel walls.

Fluorocarbon oil continuous phases are well-suited as the continuous phase for aqueous droplet libraries for a number of reasons. Fluorous oils are both hydrophobic and lipophobic. Therefore, they have low solubility for components of the aqueous phase and they limit molecular diffusion between droplets. Also, fluorous oils present an inert interface for chemistry and biology within droplets. In contrast to hydrocarbon or silicone oils, fluorous oils do not swell PDMS materials, which is a convenient material for constructing microfluidic channels. Finally, fluorocarbon oils have good solubility for gases, which is necessary for the viability of encapsulated cells.

Combinations of surfactant(s) and oils must be developed to facilitate generation, storage, and manipulation of droplets to maintain the unique chemical/biochemical/biological environment within each droplet of a diverse library. Therefore, the surfactant and oil combination must (1) stabilize droplets against uncontrolled coalescence during the drop forming process and subsequent collection and storage, (2) minimize transport of any droplet contents to the oil phase and/or between droplets, and (3) maintain chemical and biological inertness with contents of each droplet (e.g., no adsorption or reaction of encapsulated contents at the oil-water interface, and no adverse effects on biological or chemical constituents in the droplets). In addition to the requirements on the droplet library function and stability, the surfactant-in-oil solution must be coupled with the fluid physics and materials associated with the platform. Specifically, the oil solution must not swell, dissolve, or degrade the materials used to construct the microfluidic chip, and the physical properties of the oil (e.g., viscosity, boiling point, etc.) must be suited for the flow and operating conditions of the platform.

Droplets formed in oil without surfactant are not stable to permit coalescence, so surfactants must be dissolved in the fluorous oil that is used as the continuous phase for the emulsion library. Surfactant molecules are amphiphilic—part of the molecule is oil soluble, and part of the molecule is water soluble. When a water-oil interface is formed at the nozzle of a microfluidic chip for example in the inlet module described herein, surfactant molecules that are dissolved in the oil phase adsorb to the interface. The hydrophilic portion of the molecule resides inside the droplet and the fluorophilic portion of the molecule decorates the exterior of the droplet. The surface tension of a droplet is reduced when the interface is populated with surfactant, so the stability of an emulsion is improved. In addition to stabilizing the droplets against coalescence, the surfactant should be inert to the contents of each droplet and the surfactant should not promote transport of encapsulated components to the oil or other droplets.

The invention can use pressure drive flow control, e.g., utilizing valves and pumps, to manipulate the flow of cells, particles, molecules, enzymes or reagents in one or more directions and/or into one or more channels of a microfluidic device. However, other methods may also be used, alone or in combination with pumps and valves, such as electro-osmotic flow control, electrophoresis and dielectrophoresis as described in Fulwyer, Science 156, 910 (1974); Li and Harrison, Analytical Chemistry 69, 1564 (1997); Fiedler, et al. Analytical Chemistry 70, 1909-1915 (1998) and U.S. Patent No. 5,656,155. Application of these techniques according to the invention provides more rapid and accurate devices and methods for analysis or sorting, for example, because the sorting occurs at or in a sorting module that can be placed at or immediately after a detection module. This provides a shorter distance for molecules or cells to travel, they can move more rapidly and with less turbulence, and can more readily be moved, examined, and sorted in single file, i.e., one at a time.

Positive displacement pressure driven flow is a preferred way of controlling fluid flow and dielectrophoresis is a preferred way of manipulating droplets within that flow. The pressure at the inlet module can also be regulated by adjusting the pressure on the main and sample inlet channels, for example, with pressurized syringes feeding into those inlet channels. By controlling the pressure difference between the oil and water sources at the inlet module, the size and periodicity of the droplets generated may be regulated. Alternatively, a valve may be placed at or coincident to either the inlet module or the sample inlet channel connected thereto to control the flow of solution into the inlet module, thereby controlling the size and periodicity of the droplets. Periodicity and droplet volume may also depend on channel diameter, the viscosity of the fluids, and shear pressure. Examples of driving pressures and methods of modulating flow are as described in WO 2006/040551; WO 2006/040554; WO 2004/002627; WO 2004/091763; WO 2005/021151; WO 2006/096571; WO 2007/089541; WO 2007/081385 and WO 2008/063227; U.S. Pat. No. 6,540,895 and U.S. Patent Application Publication Nos. 20010029983 and 20050226742

The microfluidic device of the present invention may include one or more inlet modules. An "inlet module" is an area of a microfluidic substrate device that receives molecules, cells, small molecules or particles for additional coalescence, detection and/or sorting. The inlet module can contain one or more inlet channels, wells or reservoirs, openings, and other features which facilitate the entry of molecules, cells, small molecules or particles into the substrate. A substrate may contain more than one inlet module if desired. Different sample inlet channels can communicate with the main channel at different inlet modules. Alternately, different sample inlet channels can communication with the main channel at the same inlet module. The inlet module is in fluid communication with the main channel. The inlet module generally comprises a junction between the sample inlet channel and the main channel such that a solution of a sample (i.e., a fluid containing a sample such as molecules, cells, small molecules (organic or inorganic) or particles) is introduced to the main channel and forms a plurality of droplets. The sample solution can be pressurized. The sample inlet channel can intersect the main channel such that the sample solution is introduced into the main channel at an angle perpendicular to a stream of fluid passing through the main channel. For example, the sample inlet channel and main channel intercept at a T-shaped junction; i.e., such that the sample inlet channel is perpendicular (90 degrees) to the main channel. However, the sample inlet channel can intercept the main channel at any angle, and need not introduce the sample fluid to the main channel at an angle that is perpendicular to that flow. The angle between intersecting channels is in the range of from about 60 to about 120 degrees. Particular exemplary angles are 45, 60, 90, and 120 degrees.

Embodiments of the invention are also provided in which there are two or more inlet modules producing droplets of samples into the main channel. For example, a first inlet module may produce droplets of a first sample into a flow of fluid in the main channel and a second inlet module may produce droplets of a second sample into the flow of fluid in main channel, and so forth. The second inlet module is preferably downstream from the first inlet module (e.g., about 30 µm). The fluids produced into the two or more different inlet modules can comprise the same fluid or the same type of fluid (e.g., different aqueous solutions). For example, droplets of an aqueous solution containing an enzyme are produced into the main channel at the first inlet module and droplets of aqueous solution containing a substrate for the enzyme are produced into the main channel at the second inlet module. Alternatively, the droplets produced at the different inlet modules may be droplets of different fluids which may be compatible or incompatible. For example, the different droplets may be different aqueous solutions, or produced introduced at a first inlet module may be droplets of one fluid (e.g., an aqueous solution) whereas droplets produced at a second inlet module may be another fluid (e.g., alcohol or oil). The terms "produced" or "producing" are meant to describe forming, generating, or creating droplets from a continuous sample source. Moreover, the term producing encompasses introducing pre-formed droplets (e.g., droplets made off chip) into a microfluidic channel in a microfluidic device.

What is claimed is:

1. A method of merging droplets, comprising
    flowing a first plurality of fluidic droplets within a microfluidic channel at a first frequency;
    providing a second plurality of fluidic droplets within the microfluidic channel at a second frequency;
    capturing an image of the first plurality and/or second plurality of fluidic droplets over a plurality of pulses of illumination;
    assessing the first frequency and/or the second frequency from the captured image;
    transmitting the assessment of the first and/or the second frequencies to a feedback controller, wherein the feedback controller adjusts a flow rate of one or more fluids to provide a desired frequency ratio of the first plurality of fluidic droplets to said second plurality of fluidic droplets; and
    merging at least one of the first plurality of fluidic droplets with at least one of the second plurality of fluidic droplets within the microfluidic channel.

2. The method of claim 1, wherein the first plurality of fluidic droplets each comprise a biological library element.

3. The method of claim 1, wherein the second plurality of fluidic droplets each comprise a single primer pair.

4. The method of claim 1, wherein the second plurality of fluidic droplets are pre-made library of droplets.

5. The method of claim 1, wherein the second plurality of fluidic droplets each comprise at least a different element.

6. The method of claim 1, wherein the second plurality of fluidic droplets each comprise a different antibody species.

7. The method of claim 1, wherein the first plurality of fluidic droplets each comprise a cell.

8. The method of claim 1, wherein the first plurality of fluidic droplets each comprise an enzyme.

9. The method of claim 1, wherein the first plurality of droplets are flowing in a carrier fluid.

10. The method of claim 9, wherein the drive fluid comprise the same substance as the carrier fluid.

11. The method of claim 1, wherein the second plurality of fluidic droplet is provided at a frequency of 900 to 1100 per second.

12. The method of claim 9, wherein the feedback controller adjusts the flow rate of the carrier fluid.

13. The method of claim 10, wherein the feedback controller adjusts the flow rate of the drive fluid.

14. The method of claim 2, wherein the biological library element is selected from the group consisting of compounds, primer pairs, and antibody species.

* * * * *